United States Patent [19]
Gupta et al.

[11] Patent Number: 5,824,801
[45] Date of Patent: Oct. 20, 1998

[54] PROCESS FOR STEROSPECIFIC SYNTHESIS OF KETO-ENOL TAUTOMERIC MIXTURE OF P NITROBENZYL (1R, 6R, 7R)-7-PHENOXYACETAMIDO-3-OXO-3-CEPHAM-4-(R/S)-CARBOXYLATE-1-OXIDE AND P-NITROBENZYL (1R, 6R, 7R)-7-PHENOXYACTEAMIDO-3-HYDROXY-3-CEPHEM-4-CARBOXYLATE-1-OXIDE

[75] Inventors: Niranjan Lal Gupta; Ramanathan Sankaran; Sugata Chattejee; Tumma Hari Krishna, all of Madhya Pradesh, India

[73] Assignee: Lupin Laboratories Ltd., Bombay, India

[21] Appl. No.: 908,016

[22] Filed: Aug. 11, 1997

Related U.S. Application Data

[62] Division of Ser. No. 618,533, Mar. 19, 1996.

[30] Foreign Application Priority Data

Jan. 19, 1996 [IN] India ................................... 39/BOM/96

[51] Int. Cl.$^6$ ................................................. C07D 501/59
[52] U.S. Cl. .......................................................... 540/215
[58] Field of Search ............................................. 540/215

[56] References Cited

U.S. PATENT DOCUMENTS

| | | | |
|---|---|---|---|
| 3,691,188 | 9/1972 | Spry | 540/319 |
| 3,917,587 | 11/1975 | Chauvette | 260/243 |
| 3,925,372 | 12/1975 | Chauvette | 260/16 |
| 4,060,688 | 11/1977 | Chauvette | 544/30 |
| 4,064,343 | 12/1977 | Chauvett | 544/16 |
| 4,165,315 | 8/1979 | Kukolja | 260/239 A |
| 4,165,316 | 8/1979 | Chou | 260/239 A |
| 4,316,842 | 2/1982 | Chauvette | 260/245.2 R |
| 4,334,065 | 6/1982 | Chauvette | 544/30 |
| 4,431,803 | 2/1984 | Kukolja | 544/16 |
| 4,477,658 | 10/1984 | Scartazzini | 544/16 |
| 4,668,781 | 5/1987 | Scartazzini | 540/215 |
| 5,254,680 | 10/1993 | Alpegiani | 540/230 |
| 5,410,044 | 4/1995 | Khanna | 540/222 |
| 5,442,058 | 8/1995 | Nieuwenhuis | 540/215 |
| 5,536,830 | 7/1996 | Khanna | 540/215 |
| 5,594,130 | 1/1997 | Lim | 540/222 |
| 5,594,131 | 1/1997 | Lim | 540/222 |

OTHER PUBLICATIONS

Kobayashi, M. "Synthesis of 7–B–C(2)–2–(2–Amino . . ." Chem Pharm. Bull, vol. 36, pp. 582–591 (1988).

Bremmer, D.H. "A Stereoselective Synthesis . . . " J. Chem. Research (5) 1992, 422–423.

Spry, D.O. "Oxidation of Penicillin . . . ", J. Org. Chem. vol. 37, (5) pp. 793–795 (1972).

Scartazzini, R. "Neue B–Lactam . . . " Helvetica Chimica Acta, vol. 57, Fase, 7 (1974) Nr. 208–209.

Chauvette, R.R. et al., "Chemistry of Cephalosporin . . . " J. Med. Chem. 18(4) 403–408 (1975).

Scartazzini, R. "New Orally Active Cephalosproins" Heterocycles, vol. 7, No. 2, 1977.

*Primary Examiner*—John M. Ford
*Attorney, Agent, or Firm*—Ladas & Parry

[57] ABSTRACT

A process for the stereospecific synthesis of keto-enol tautomeric mixture of p-nitrobenzyl (1R,6R,7R)-7-phenoxyacetamido-3-oxo-3-cepham-4-(R/S)-carboxylate-1-oxide and p-nitrobenzyl (1R,6R,7R)-7-phenoxyacetamido-3-hydroxy-3-cephem-4-carboxylate-1-oxide is described. These compounds are valuable intermediates for the synthesis of cephalosporin antibiotics e.g. cefaclor.

12 Claims, 9 Drawing Sheets

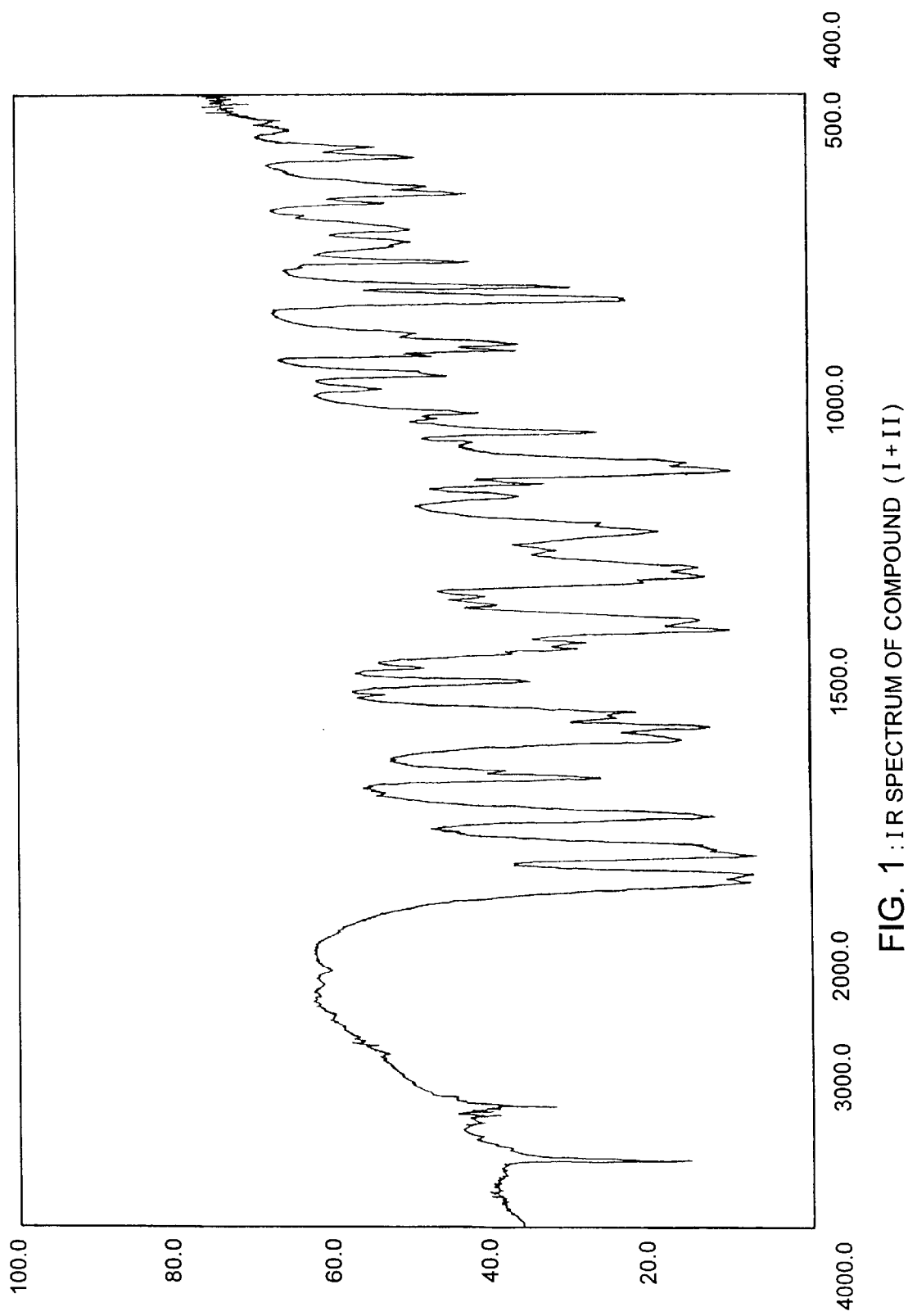
FIG. 1 : IR SPECTRUM OF COMPOUND (I+II)

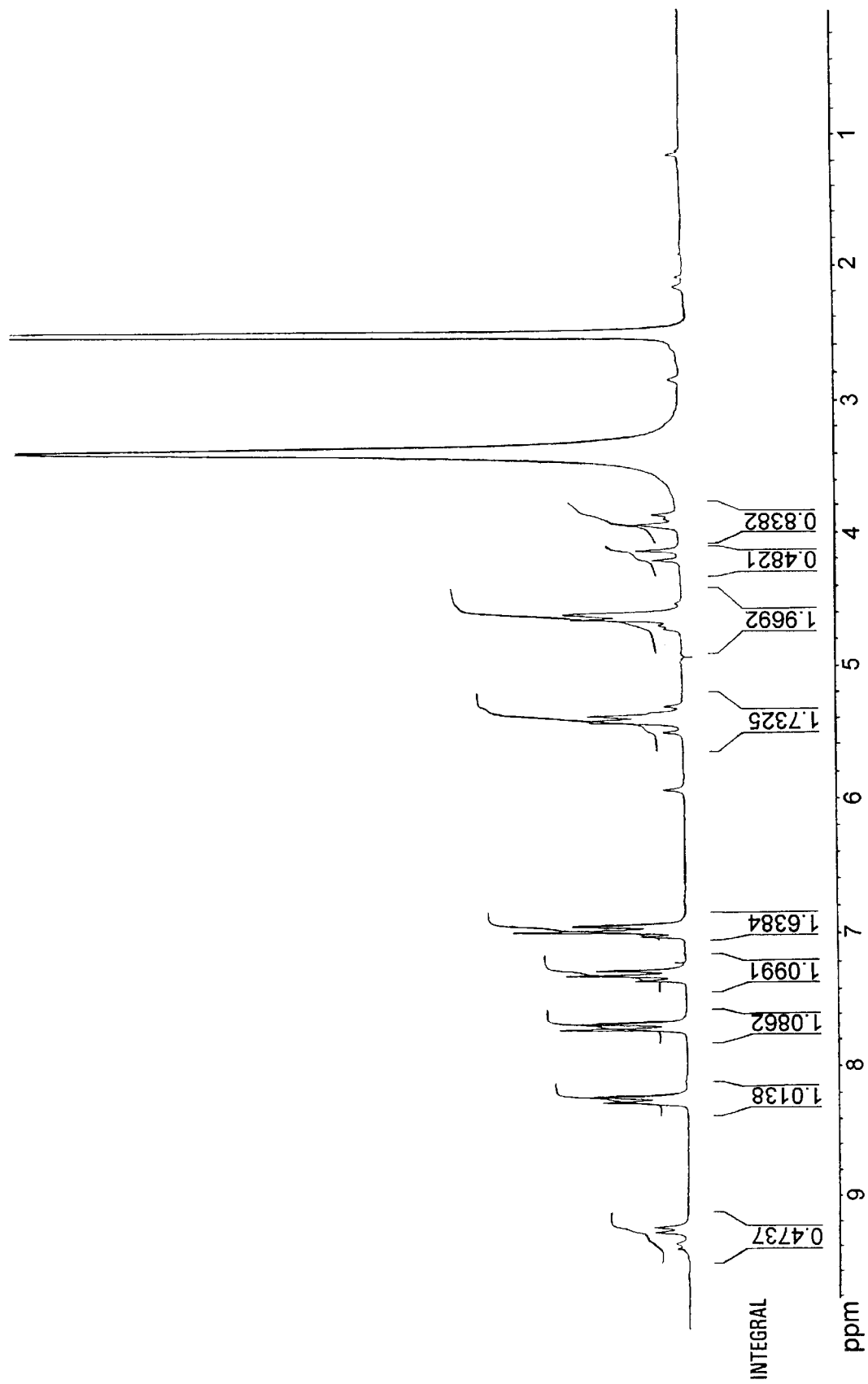
FIG. 2: PROTON NMR SPECTRUM OF COMPOUND (I + II) IN DMSO-d6

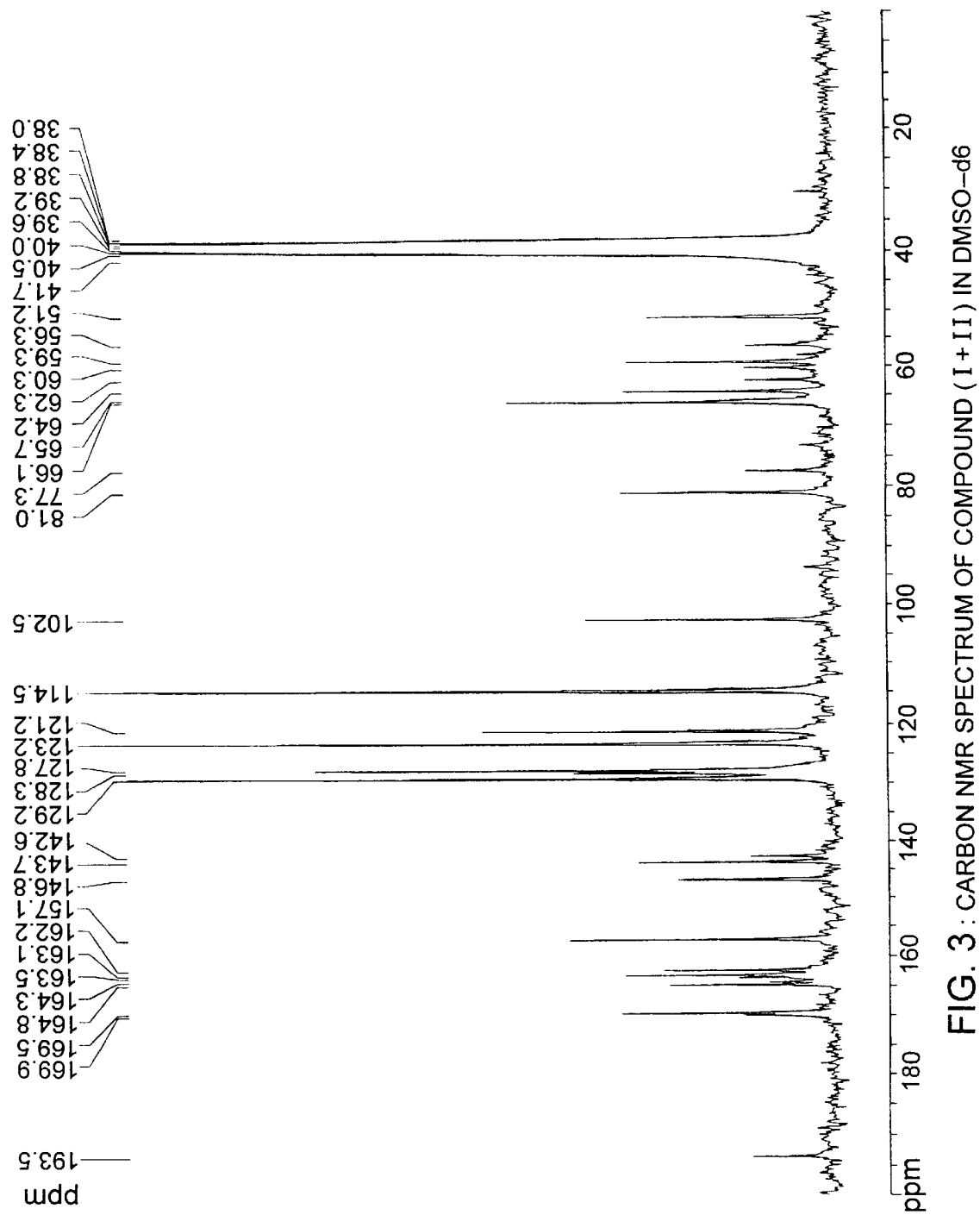
FIG. 3 : CARBON NMR SPECTRUM OF COMPOUND (I + II) IN DMSO-d6

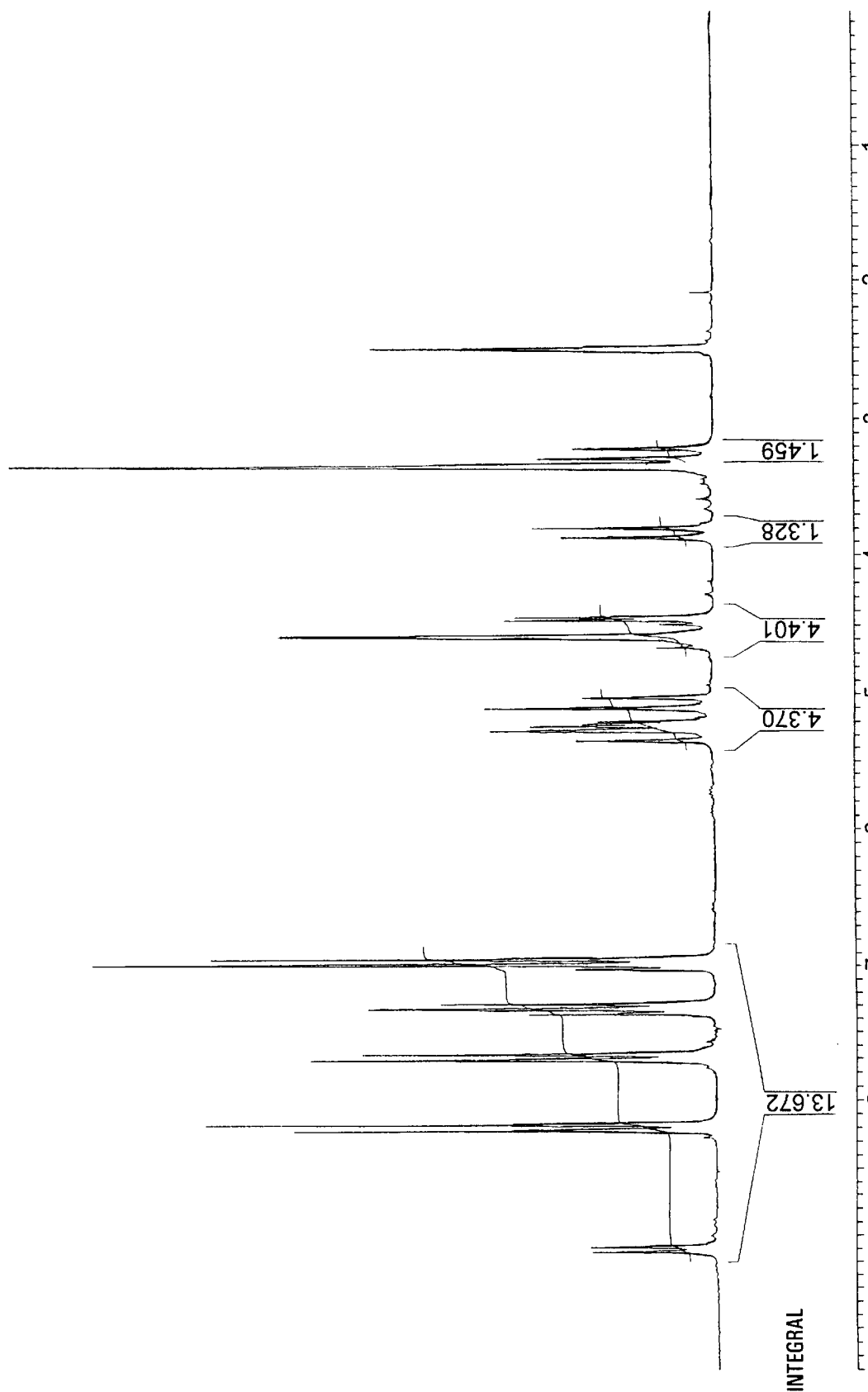
FIG. 4: PROTON NMR SPECTRUM OF COMPOUND 1a IN DMSO-d6

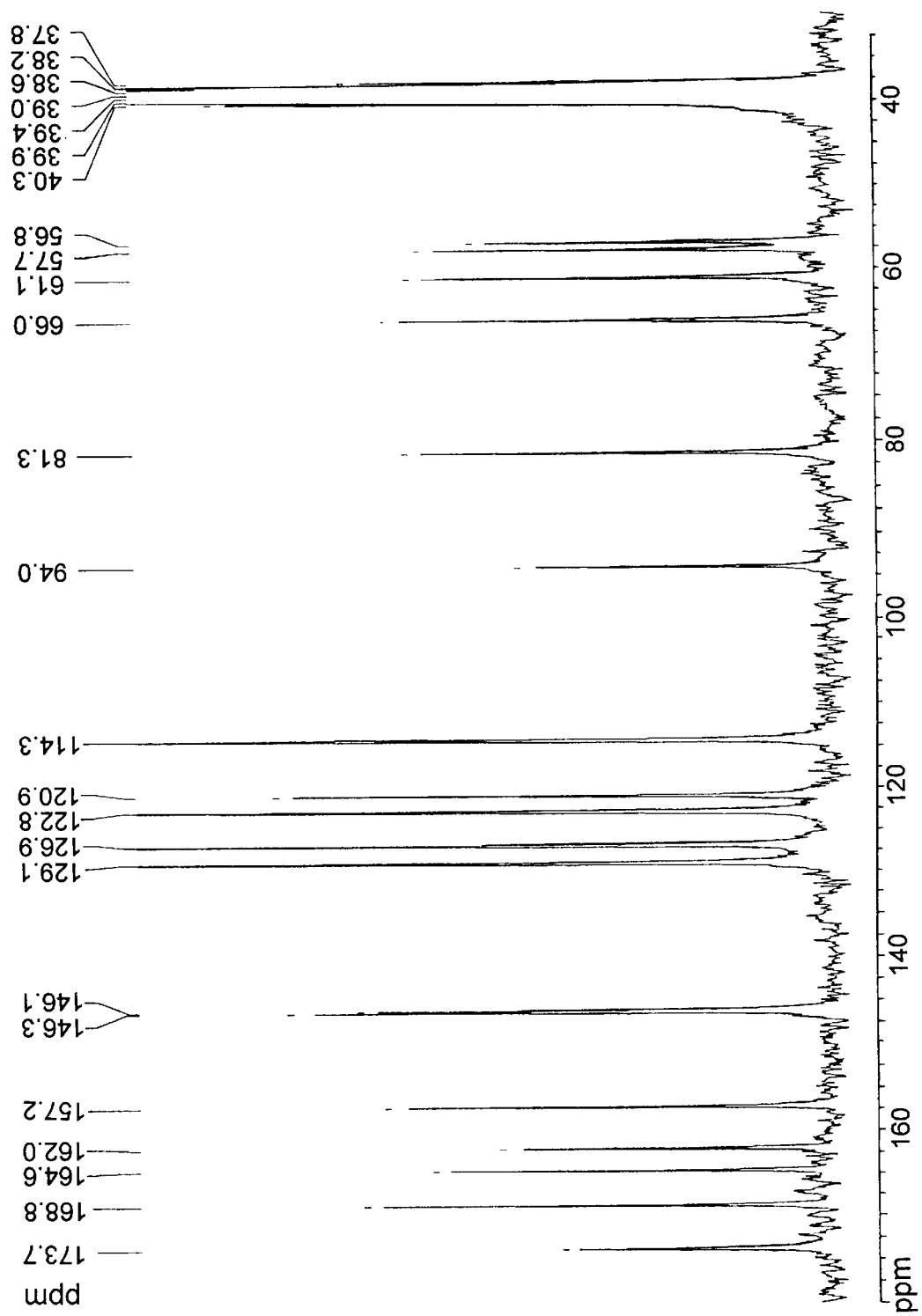
FIG. 5: CARBON NMR SPECTRUM OF COMPOUND 1a IN DMSO-d6

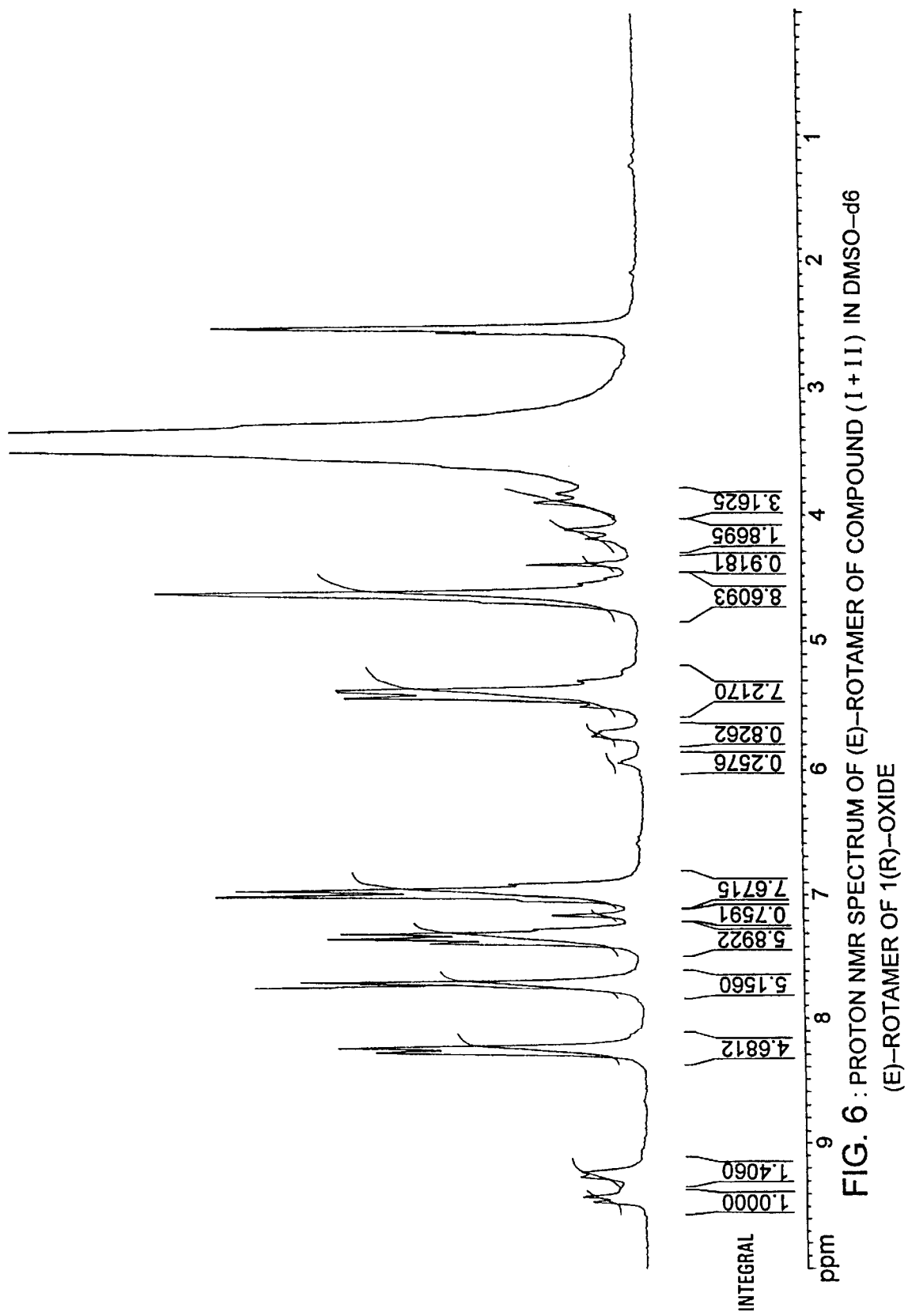
FIG. 6: PROTON NMR SPECTRUM OF (E)-ROTAMER OF COMPOUND (I + II) IN DMSO-d6 (E)-ROTAMER OF 1(R)-OXIDE

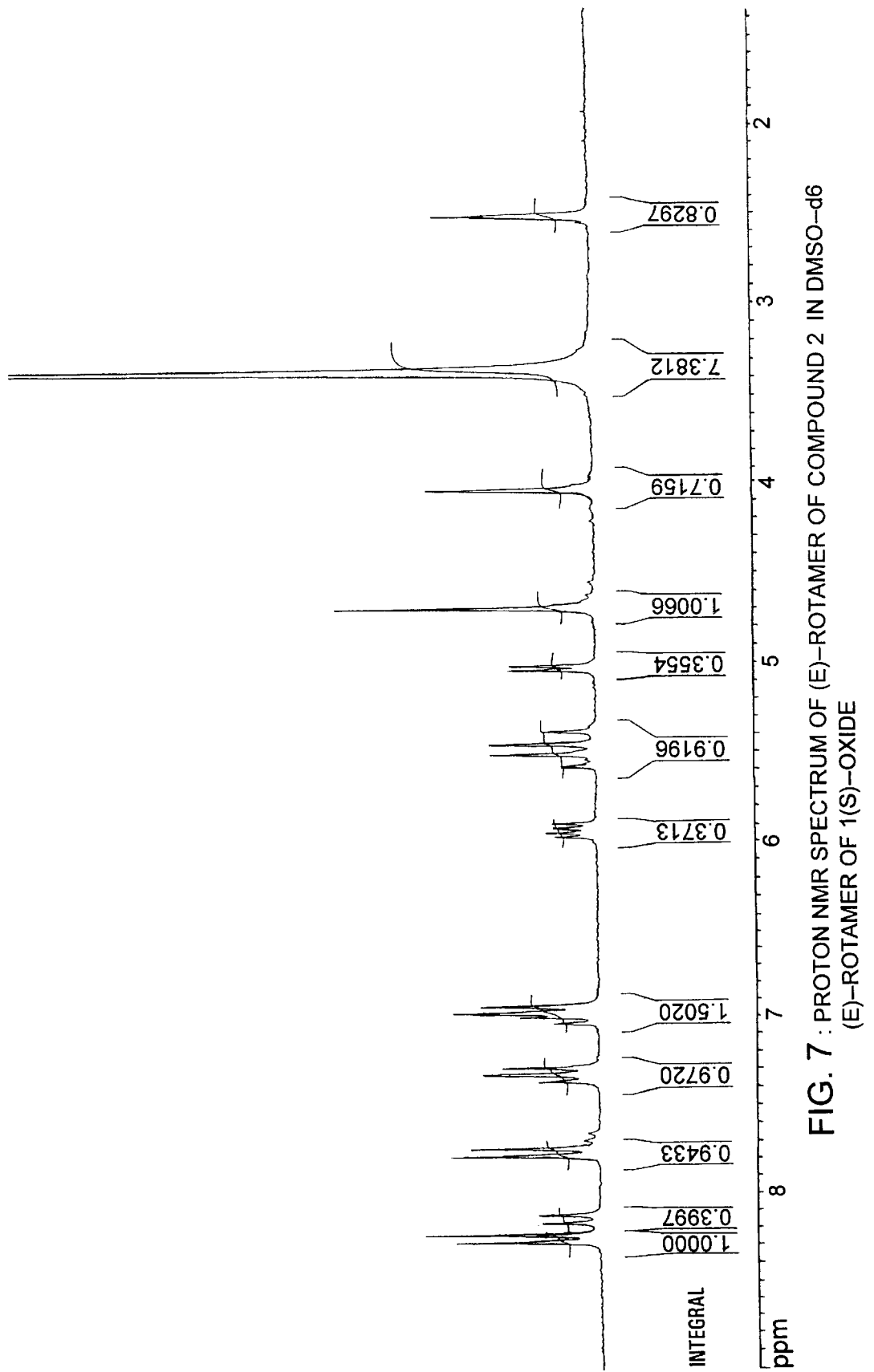
FIG. 7: PROTON NMR SPECTRUM OF (E)-ROTAMER OF COMPOUND 2 IN DMSO-d6 (E)-ROTAMER OF 1(S)-OXIDE

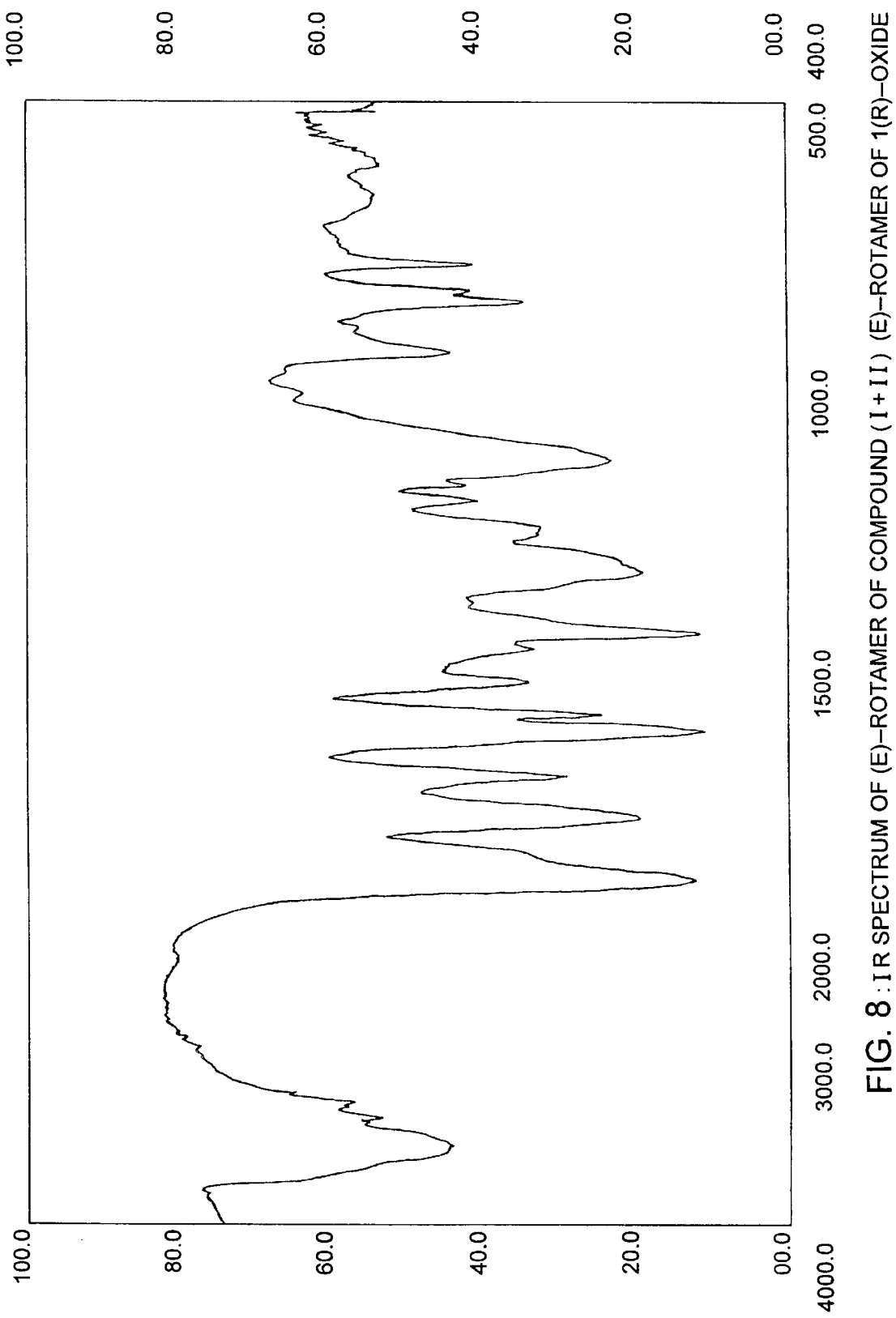
FIG. 8: IR SPECTRUM OF (E)-ROTAMER OF COMPOUND (I+II) (E)-ROTAMER OF 1(R)-OXIDE

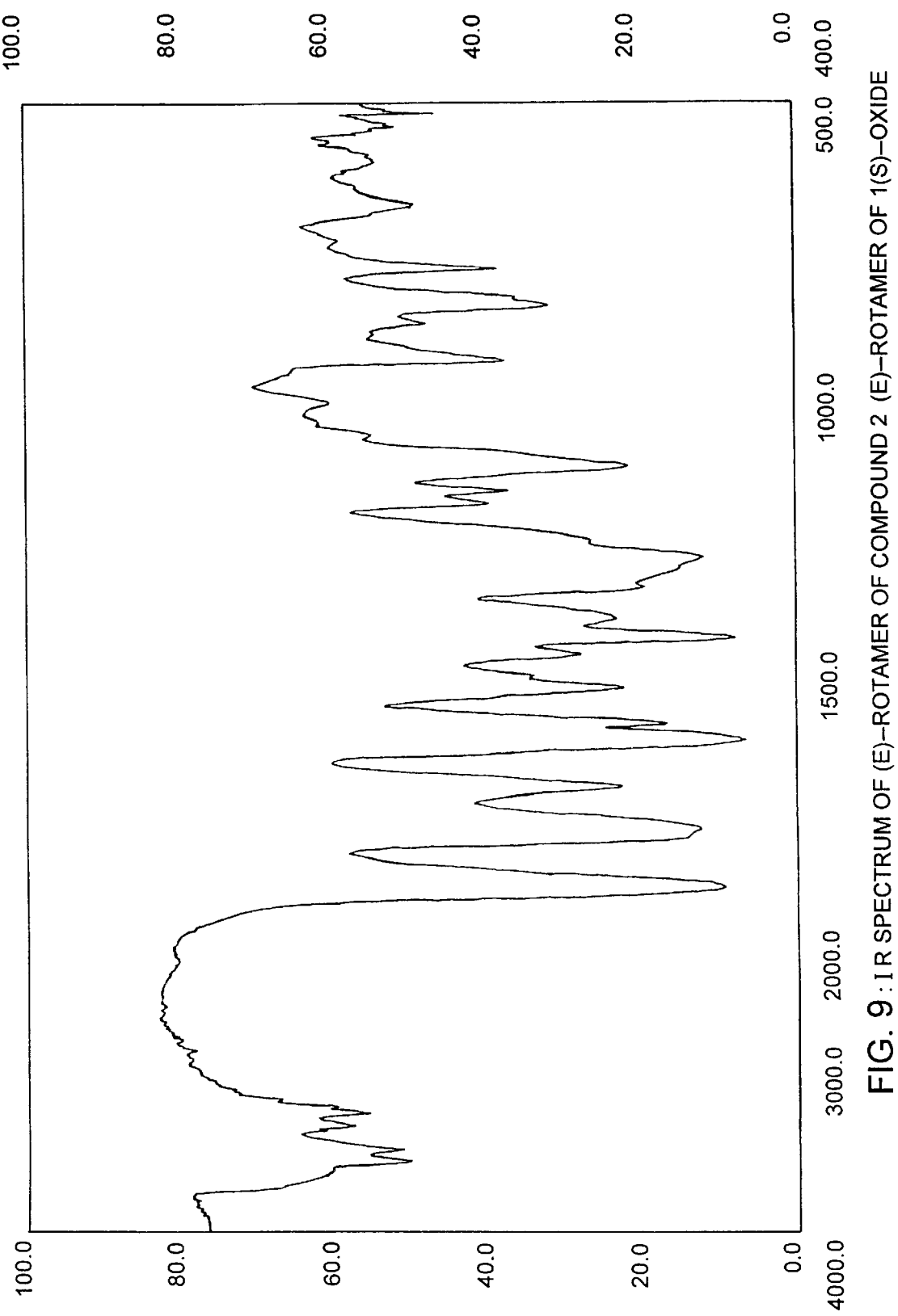
FIG. 9: IR SPECTRUM OF (E)-ROTAMER OF COMPOUND 2 (E)-ROTAMER OF 1(S)-OXIDE

PROCESS FOR STEROSPECIFIC SYNTHESIS OF KETO-ENOL TAUTOMERIC MIXTURE OF P NITROBENZYL (1R, 6R, 7R)-7-PHENOXYACETAMIDO-3-OXO-3-CEPHAM-4-(R/S)-CARBOXYLATE-1-OXIDE AND P-NITROBENZYL (1R, 6R, 7R)-7-PHENOXYACTEAMIDO-3-HYDROXY-3-CEPHEM-4-CARBOXYLATE-1-OXIDE

This is a divisional of application Ser. No. 08/618,533 filed on Mar. 19, 1996.

A process for the stereospecific synthesis of keto-enol tautomeric mixture of p-nitrobenzyl (1R,6R,7R)-7-phenoxyacetamido-3-oxo-3-cepham-4-(R/S)-carboxylate-1-oxide and p-nitrobenzyl (1R,6R,7R)-7-phenoxyacetamido-3-hydroxy-3-cephem-4-carboxylate-1-oxide.

BACKGROUND OF THE INVENTION

This invention relates to a process for the stereospecific synthesis of a keto-enol tautomeric mixture of p-nitrobenzyl (1R,6R,7R)-7-phenoxyacetamido-3-hydroxy-3-cephem-4-carboxylate-1-oxide and p-nitrobenzyl (1R,6R,7R)-7-phenoxyacetamido-3-oxo-3-cepham-4-(R/S)-carboxylate-1-oxide ("TITLE COMPOUND") which are represented by formula I and II respectively.

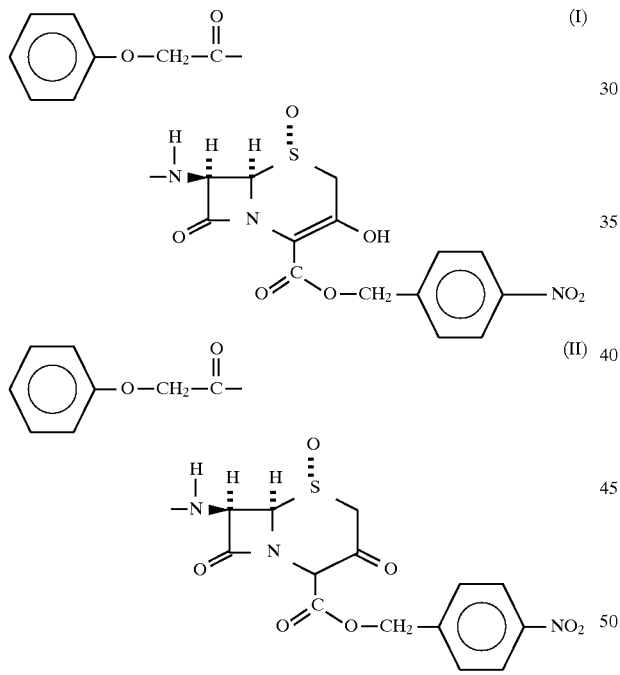

The compounds (I+II) are useful intermediates for preparing cephalosporin antibiotics e.g. cefaclor. In the literature several methods are reported for the ozonolysis of the 3-exomethylene-cepham compound to the corresponding 3-keto(enol) cepham compound, the description of the prior art is as follows:

A) In the Helv. Chim. Acta, 57,1919 (1974) the preparation of 7-acylamido-3-hydroxy-3-cephem-4-carboxylates (IV) is described in which 7-acylamido-3-methylene-cepham compounds (III) are ozonized in methylene chloride at −70° C. followed by reduction of the resulting ozonide with dimethyl sulfide to yield about 40–50% of IV. Also reported is the formation of sulfoxides V and VI. However neither the stereochemistry of the sulfoxides nor the exact amounts in which the products are obtained is revealed. The above process is illustrated in the following scheme A.

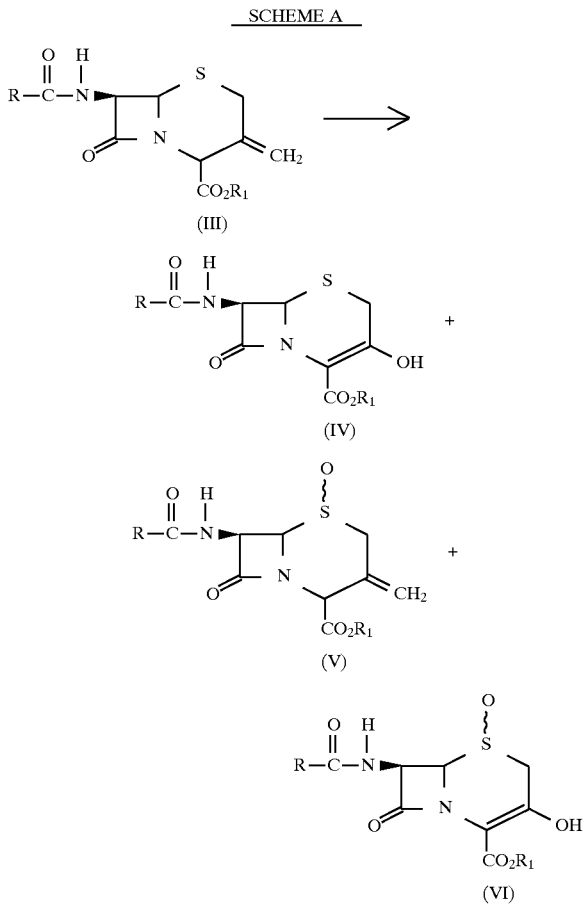

Wherein R = $C_6H_5CH_2$, $C_6H_5OCH_2$, $C_6H_5CH(NHCO_2CMe_3)$, $R_1$ = $CHPh_2$ B) The ozonolysis of 3-methylene-cepham compound to obtain 3-hydroxycephem ester is briefly reported in Heterocycles, 7,1165 (1977)

C) Chauvette and Pennington in J. Med. Chem, 18,403 (1975) disclosed the ozonolysis of 7-amino or 7-acylamido-cepham derivatives at low temperature followed by reduction of the resulting ozonide with sodium bisulfite to yield the corresponding 7-amino and 7-acylamido-3-hydroxy-3-cephem compounds in 75% and 30–42% yield respectively. It was revealed that although the oxidative cleavage of the 3-exomethylene function in the 7-acylamido derivatives was complex, the ozonolysis of the C-7 free amino derivative was facile.

D) In J. Org. Chem., 37,793–5 (1972), Spry described the ozonolysis of cephalosporin derivatives in acetone-water mixture to obtain a mixture of alpha- and beta-sulfoxides in which alpha-sulfoxide predominates, only when the double bond at 3-position is hydrogenated prior to ozonolysis. With the double bond at C-3 position, ring cleavage is the preferred reaction.

E) In Chem Pharm Bull, 36(2), 582–591 (1988), the preparation of 7-amino-3-hydroxy-3-cephem-4-carboxylic acid (IX) is described in which 7-amino-3-exomethylene-cepham-4-carboxylic acid (VII) was ozonized in methanol at −75° C. to yield the corresponding 3-hydroxy-3-cephem compound (VIII) which is further reduced with NaBH4 to yield 83% of (IX). It was also observed that when 7-phenylacetamido-3-methylene-cepham-4-carboxylic acid (X) was ozonized in methylene chloride, the desired 3-hydroxy-3-cephem compound (XI) was not obtained, but when ozonolysis of (X) was carried out in methanol at −65° C. followed by treatment of the reaction mixture with excess of diphenyl diazomethane the ester (XII) was obtained. The above process is illustrated in the following Scheme B:

ably from the corresponding 7-Acylamido-3-exomethylene -cepham-4-carboxylate-1-beta oxide. No diastereo specific synthesis of the diastereoisomer of the present invention has been described.

Thus, it would be evident from the prior art that:
i) Ozonolysis of 3-exomethylene-cepham carboxylates gave the corresponding 3-keto-cepham carboxylates as the major product.
ii) Ozonolysis of 3-exomethylene-cepham-1-oxide-4-carboxylates gave the corresponding 3-hydroxy-3-cephem-1-oxide-4-carboxylates and since in the

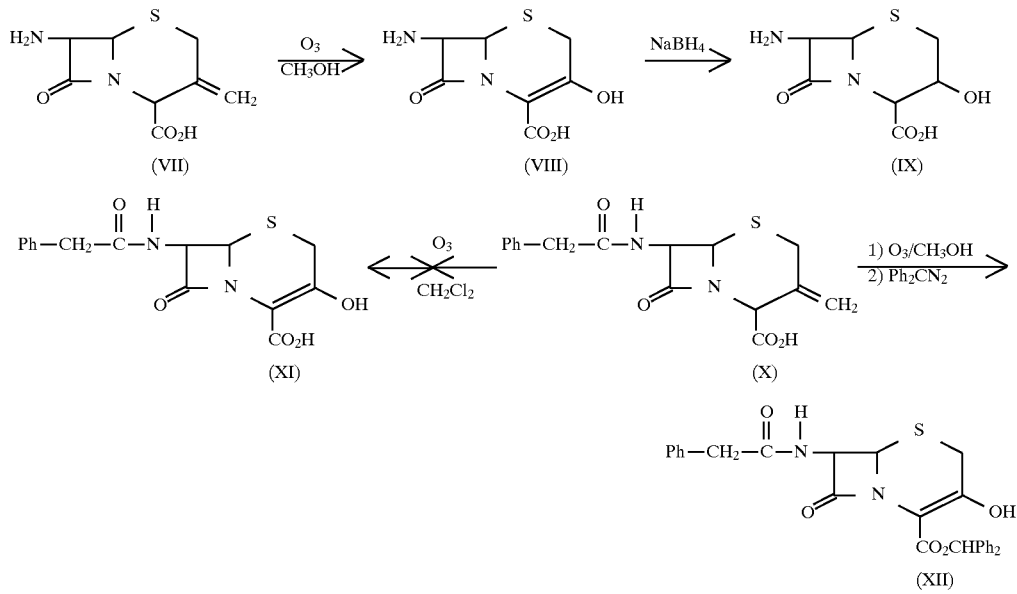

F) U.S Pat. Nos. 3,917,587, 3,925,372, 4,064,343, 4,060,688 describe the ozonization of the 7-amino or 7-acylamido-3-exomethylene-cepham-4-carboxylic acid esters in solvents like methylene chloride, methanol, ethyl acetate etc., at a temperature range of −80° C. and −50° C. and the resulting ozonide is always decomposed with a reducing agent such as sodium bisulfite, sulphur dioxide and trimethylphosphite to afford the corresponding 3-hydroxy-3-cephem-4-carboxylic acid esters. Also mentioned is the formation of sulfoxide side products, the 3-exomethylene sulfoxide ester and the 3-hydroxy-3-cephem ester. The formation of the sulfoxides is said to occur as a result of over oxidation in the ozonolysis reaction.

G) U.S. Pat. Nos. 4,477,658, 4,668,781 and CA 1 110 231, disclose the ozonolysis of 7-amino or 7-acylamido-3-exomethylene-cepham-4-carboxylates and their 1-oxides. For instance, 7-acylamido-3-exomethylene-cepham-4-carboxylate is converted mainly to the corresponding 7-acylamido-3-hydroxy-3-cephem-4-carboxylate and the compound, 7-acylamido-3-exomethylene-cepham-4-carboxylate-1-oxide is obtained as a co-product. The 7-acylamido-3-exomethylene-cepham-4-carboxylate-1-oxide gives the corresponding 3-hydroxy-3-cephem compound.

U.S. Pat. No. 4,668,781 and 5,410,044 describe the synthesis of 7-Acylamido-3-hydroxy-3-cephem-4-carboxylate-1-beta oxide by ozonisation in methylene chloride, ethylacetate, acetonitrile, methanol presumprior art oxidation of the ring sulfur atom of the cephalosporin or starting pencillin was carried out with peracids, the stereochemistry of the ring sulfoxide group was beta not alpha.
iii) Ozonolysis of the 3-exomethylene-cepham carboxylates produced undetermined quantities of the corresponding 3-keto-cepham-1-oxide carboxylates as a mixture of the 1-R and 1-S diastereoisomers. The isolation of the latter was tedious and not practical.
iv) There is no mention of the stereospecific synthesis of p-nitrobenzyl (1R,6R,7R)-7-phenoxyacetamido-3-oxo-3-cepham-4-carboxylate and its enol tautomer in the prior art, but what has been reported is a practical synthesis of the other diastereoisomer viz p-nitrobenzyl (1S,6R,7R)-7-phenoxyacetamido-3-oxo-3-cepham-4-carboxylate, Z and E rotamers, which exists essentially in the enol form.

In the prior art, the intermediate ozonide formed from the substrate, 7-amino or 7-acylamido-3-exomethylene-cepham-4-carboxylates or 1-oxide thereof, is decomposed with the aid of a reducing agent such as dimethylsulfide, sulfur dioxide, triphenyl-phosphite, sodium bisulfite, tetracyano ethylene or pyridine.

SUMMARY OF THE INVENTION

A process for the stereospecific synthesis of keto-enol tautomeric mixture of p-nitrobenzyl (1R,6R,7R)-7- phenoxyaetamido-3-oxo-3-cepham-4-(R/S)-carboxylate-1-oxide and p-nitrobenzyl (1R,6R,7R)-7-phenoxyacetamido-3-hydroxy-3-cephem-4-carboxylate-1-oxide (this tautomeric mixture will be referred to as "Title Compound") which comprises:

a) reaction of 7-phenoxyacetamido-3-exomethylene-cepham-4-carboxylic acid p-nitrobenzyl ester with ozone in a inert solvent such as acetone or methylethyl ketone, optionally in the presence of a protic solvent such as methanol, acetic acid or isopropanol at a temperature ranging from −90° C. to −40° C. to give the corresponding ozonide and, b) decomposition of the ozonide to the Title Compound without any reducing agent. The Title Compound is a valuable intermediate for the synthesis of cephalosporin antibiotics e.g. cefaclor.

BRIEF DESCRIPTION OF THE DRAWINGS

FIG. I: illustrates the characteristic IR spectrum of compound (I+II).

FIG. II: illustrates proton NMR spectrum of compound (I+II).

FIG. III: illustrates carbon NMR spectrum of compound (I+II)

FIG. IV: illustrates proton NMR spectrum of compound Ia.

FIG. V: illustrates carbon NMR spectrum of compound Ia.

FIG. VI: illustrates proton NMR spectrum of E-Rotamer of compound (I+II) in DMSO-$d_6$ FIG. VII: illustrates proton NMR spectrum of E-Rotamer of compound 2 in DMSO-$d_6$.

FIG. VIII: illustrates IR spectrum of E-Rotamer of compound (I+II).

FIG. IX: illustrates IR spectrum of E-Rotamer of compound 2.

DETAILED DESCRIPTION

This invention describes a diastereospecific synthesis of a mixture of p-nitrobenzyl (1R,6R,7R)-7-phenoxyacetamido-3-hydroxy-3-cephem-4-carboxylate-1-oxide(I) and its tautomer (Ii) in high yields by ozonisation of p-nitrobenzyl (6R,7R)7-phenoxyacetamido-3-exomethylene-cepham 4-carboxylate(III) (R=$C_6H_5OCH_2$; R1 is p-nitrobenzyl) and whose isolation is a simple operation. Compounds I and II are new compounds.

The present invention relates to a process for the stereospecific synthesis of keto-enol tautomeric mixture of p-nitrobenzyl (1R,6R,7R)7-phenoxyacetamido-3-oxo-3-cepham-4-(R/S)-carboxylate-1-oxide(II) and p-nitrobenzyl (1R,6R,7R)-7-phenoxyacetamido-3-hydroxy-3-cephem-4-carboxylate-1-oxide(I) which comprises of reaction of p-nitrobenzyl phenoxyacetamido-3-exomethylene-cepham-4-carboxylate(III) with ozone in a inert solvent such as acetone or methylethyl ketone, optionally in the presence of a protic solvent such as methanol, acetic acid or isopropanol at a temperature ranging from −90° C. to −40° C. to give the corresponding ozonide and subsequent decomposition of the resulting ozonide to Title Compound without any reducing agent. A mixture of inert solvents may be used. When two inert solvents are used it is preferred that they be used in a ratio of 1:1 to 1:9.

The Title Compound is a valuable intermediate for the synthesis of cephalosporin antibiotics e.g cefaclor.

The ozonisation of III is carried out in an inert solvent selected from acetone or methylethyl ketone, preferably in the presence of a protic solvent like methanol, acetic acid or isopropanol at −90° C. to −40° C. the ratio of inert solvent to protic solvent is 120:1 to 30:1 preferably in the ratio of 40:1.

The other aspect of the present invention is that the intermediate ozonide resulting from the reaction of III(R= $C_6H_5OCH_2$, R1=p-nitrobenzyl) with ozone, is decomposed to compounds I and Ii at low temperatures even without use of any reducing agent like divalent or tetravalent sulfur compounds, trivalent phosphorous compounds, pyridine or tetracyano ethylene.

The process of the present invention was carried out by ozonisation of 7-phenoxyacetamido-3-exomethylene-cepham-4-carboxylic acid p-nitrobenzyl ester (III) in a mixture of acetone and a protic solvent such as methanol, acetic acid or isopropanol in a ratio ranging from 120:1 to 30:1, preferably in the ratio of 40:1 at a temperature ranging from −90° C. to −40° C. to yield a mixture of p-nitrobenzyl (1R,6R,7R)-7-phenoxyacetamido-3-hydroxy-3-cephem-4-carboxylate-1-oxide(I) and p-nitrobenzyl (1R,6R,7R)-7-phenoxyacetamido-3-oxo-3-cepham-4-carboxylate-1-oxide (II) in a ratio of normally about 3:1.

This reaction is carried out in a solvent media such as acetone, methylethyl ketone and dichloromethane preferably in the presence of a protic solvent such as methanol, acetic acid or isopropanol. However, the use of protic solvents is optional. The most preferred solvents of the present invention are acetone and methyl ethyl ketone. It has been observed that although the reaction can be carried out in dichloromethane, the yield of the final product(I+II) is lower as compared to that obtained in acetone.

The reaction is effectively carried out at a temperature ranging from −90° C. to −40° C. and preferably between −90° C. to −65° C.

It is our observation that ozonisation only in acetone doped with methanol or acetic acid, gives only alpha-sulfoxide-3-hydroxy/3-oxo compound. Solvents like acetonitrile, methylene chloride, ethyl acetate etc., gives predominantly beta-sulfoxide.

Interestingly, the beta sulfoxide which is generally obtained by the peracid oxidation of the sulfide of penicillin or cephalosporin exists only in the enol form but the alpha sulfoxide i.e. 3-hydroxy-3-cephem-1R-sulfoxide exist in the keto-enol tautomeric form. The melting point of the pure alpha-sulfoxide-3-hydroxy/3-oxo compound, i.e. the isomers obtained in the present invention is 196°–197° C. and the corresponding beta-sulfoxide (the sulfoxide reported in Ciba-Geigy patents U.S. Pat. Nos. 4,477,658 and 4,668,781) has a melting point of 171°–173° C. Both have distinct NMR spectra but same mass number in mass spectrum.

Thus, it is evident from the above discussion that, the object compound of the present invention i.e. p-nitrobenzyl (1R,6R,7R)-7-phenoxyacetamido-3-hydroxy-3-cephem-1-oxide-4-carboxylate(I) existing in equilibrium with its 3-oxo tautomer(II) is a novel compound hitherto not reported in the literature.

The physico-chemical and NMR spectroscopic characteristics of various compounds having the structures (I+II), Ia, 2, 2a, 3, 3a, 4 & 4a are tabulated in table I and II respectively.

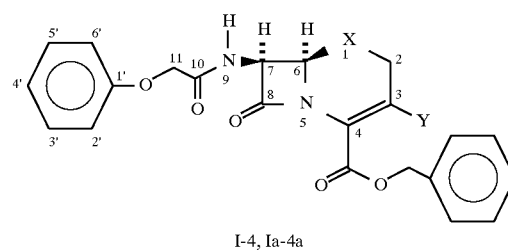

I-4, Ia-4a

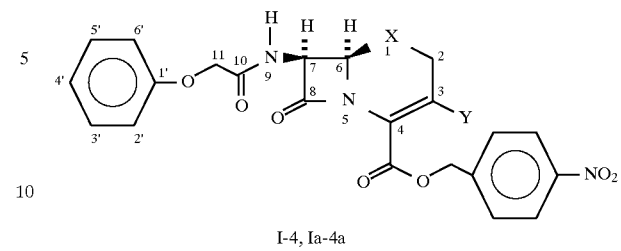

I-4, Ia-4a

| Sr. No. | Compound No. | X | Y |
|---|---|---|---|
| (i) | I | S---O (Alpha Sulfoxide) | OH |
| (ii) | Ia | S---O (Alpha Sulfoxide) | ONa |
| (iii) | 2 | S=O (Beta Sulfoxide) | OH |
| (iv) | 2a | S=O (Beta Sulfoxide) | ONa |
| (v) | 3 | $SO_2$ | OH |
| (vi) | 3a | $SO_2$ | ONa |
| (vii) | 4 | S | OH |
| (viii) | 4a | S | ONa |

TABLE I

PHYSICO CHEMICAL PROPERTIES OF COMPOUNDS (I + II)–4 AND Ia–4a

| Properties | I + II | Ia | 2 | 2a |
|---|---|---|---|---|
| Nature | White crystalline solid | Pale yellow crystals | White crystalline solid | Orange crystals |
| Solubility | | | | |
| i) Soluble in: | DMF, DMSO | H2O, DMSO, DMF | DMF, DMSO | H2O, DMSO, DMF |
| ii) Partially soluble in | Acetone, CH2Cl2, CH3OH | — | — | — |
| iii) Insoluble in: | H2O, Hexane | Acetone, CH2Cl2 CH3OH | Acetone, CH2Cl2, CH3OH, H2O, Hexane | Acetone, CH2Cl2, CH3OH |
| Molecular Weight | 501 | 522 | 501 | 522 |
| Mass: m/z | 500 $(M-1)^+$ | — | 502 $(M+H)^+$ | — |
| Molecular Formula | C22H19N3O9S | C22H18N3O9SNa | C22H19N3O9S | C22H18N3O9SNa |
| Melting Point[a] (°C.) | 196–197 | 193–196 | 171–173 | 103–106 |
| Specific Rotation[b] | | | | |
| $[\alpha]_D^{20}$ (1% solution in:) | −80.7° (DMF) | −19.09° (H2O) | +27.2° (DMF) | +102.44° (H2O) |
| $[\alpha]_D^{25}$ (1% solution in:) | −75.8° (DMF) | −18.84° (H2O) | +26.4° (DMF) | +102.35° (H2O) |
| HPLC Retention time[c] (in minutes) | 5.64 | 5.64 | 6.77 | 6.77 |
| IR[d] (KBr) (in microns) | | | | |
| NH streching | 2.93 | — | 3.02 | — |
| CH streching | 3.41 | — | 3.40 | — |
| C=O streching | 5.61, 5.62, 5.74, 5.98 | — | 5.63, 5.80, 5.95 | — |
| S→O streching | 9.41 | — | 9.63 | — |
| UV[e] (in nm) | | | | |
| λ max | 269.1, 197.3 (Aq. CH3CN) | 285.0, 193.6 (H2O) | 275.5, 198.0 (Aq. CH3CN) | 293.6, 194.0 (H2O) |
| ε | 13334, 32096 (Aq. CH3CN) | 17012, 49533 (H2O) | 15711, 32590 (Aq. CH3CN) | 17964, 49952 (H2O) |
| Properties | 3 | 3a | 4 | 4a |
| Nature | White amorphous solid | Yellow crystals | White amorphous solid | Yellow crystals |

TABLE I-continued

PHYSICO CHEMICAL PROPERTIES OF COMPOUNDS (I + II)–4 AND Ia–4a

Solubility

| | | | | |
|---|---|---|---|---|
| i) Soluble in: | Acetone, CH2Cl2, DMF, DMSO | H2O, DMSO, DMF | Acetone, CH2Cl2, DMF, DMSO, CH3OH, CH3CN | H2O, DMSO, DMF |
| ii) Partially soluble in | — | — | — | — |
| iii) Insoluble in: | H2O, Hexane | Acetone, CH2Cl2 | H2O, Hexane | Acetone, CH2Cl2 |
| Molecular Weight | 517 | 539 | 485 | 507 |
| Mass: m/z | 518 (M + H)+ | — | — | — |
| Molecular Formula | C22H19N3O10S | C22H18N3O10SNa | C22H19N3O8S | C22H18N3O8SNa |
| Melting Point[a] (°C.) | 100–103 | 157–160 | 109–111 | — |
| Specific Rotation[b] | | | | |
| [α]$_D^{20}$ (1% solution in:) | −38.82° (DMF) | — | +182.7° (DMF) | — |
| [α]$_D^{25}$ (1% solution in:) | −38.22° (DMF) | — | +181.4° (DMF) | — |
| HPLC Retention time[c] (in minutes) | 15.01 | 15.01 | 11.32 | 11.32 |
| IR[d] (KBr) (in microns) | | | | |
| NH streching | 2.94 | — | 3.00 | — |
| CH streching | 3.37 | — | 3.41 | — |
| C=O streching | 5.56, 5.93, 6.24 | — | 5.61, 5.93, 6.24 | — |
| S→O streching | — | — | — | — |
| UV[e] (in nm) | | | | |
| λ max | 275.2, 197.3 (Aq. CH3CN) | — | 269.8, 198.1 (Aq. CH3CN) | — |
| ε | 15136, 32760 (Aq. CH3CN) | — | 13797, 31293 (Aq. CH3CN) | — |

[a]Uncorrected.
[b]Recorded on Jasco DIP-370 Polarimeter.
[c]Analysis done using 4 u, C18, Novapak (3.9 × 150 mm) column using 35:65 CH3CN:H2O containing 1.5% TBAOH, pH 7.0 by H3PO4, flow rate 1.5 ml/minute, detection at 270 nm.
[d]Recorded on Perkin Elmer-1650 FTIR-Spectrophotometer.
[e]Recorded on Shimadzu-2100 UV-Spectrophotometer.

TABLE II

NMR Spectral Properties[a] Of Compounds Ia–4a

| | $^1$H NMR δH (Multiplicity, J in Hz) | | | | $^{13}$C NMR[b] δC | | | |
|---|---|---|---|---|---|---|---|---|
| Position | Ia | 2a | 3a | 4a | Ia | 2a | 3a | 4a |
| 2 | 3.26 (d, 14.67) 3.85 (d, 14.18) | 3.17 (d, 17.20) 3.55 (d, 17.20) | 3.51 (d, 14.63) 4.57 (d, 14.63) | 2.45 (d, 13.92) 3.44[e] | 56.8 | 50.7 | 61.4[f] | 35.9 |
| 3 | — | — | — | — | 162.9 | 161.9 | 162.7 | 164.3 |
| 4 | — | — | — | — | 94.0[d] | 95.6[d] | 92.1[d] | 94.7[d] |
| 5 | 4.45 (d, 4.40) | 4.94 (d, 4.39) | 4.68 (d, 4.39) | 4.98–5.19 (m) | 81.3 | 66.8 | 70.9 | 63.9 |
| 7 | 5.24 (dd, 4.40, 7.40) | 5.62 (dd, 4.39, 8.78) | 5.45 (dd, 4.39, 8.05) | 4.98–5.19 (m) | 57.7 | 54.5 | 58.0 | 59.9 |
| 8 | — | — | — | — | 164.6 | 163.0 | 164.9 | 164.3 |
| 10 | — | — | — | — | 173.7 | 167.6 | 172.0 | 169.1 |
| 11 | 4.53 (d, 15.65) 4.64 (d, 15.90) | 4.66 (s) | 4.50 (d, 13.25) 4.61 (d, 13.24) | 4.58 (d, 12.65) 4.70 (d, 12.65) | 66.0 | 66.4 | 66.4 | 67.6 |
| 4-COO— | — | — | — | — | 168.8 | 167.6 | 168.4 | 169.1 |
| 1' | 5.05 (d, 15.60) 5.31 (d, 15.61) | 5.07 (d, 16.10) 5.34 (d, 16.10) | 5.18 (d, 15.37) 5.35 (d, 15.37) | 5.28 (d, 15.18) 4.98–5.19 (m) | 61.1 | 61.8 | 61.4 | 62.2 |
| 1''' | — | — | — | — | 146.1[c] | 146.3 | 146.3 | 147.6 |
| 2''', 6''' | 7.68 (d, 8.78) | 7.65 (d, 8.79) | 7.68 (d, 8.71) | 7.65 (d, 7.88) | 126.9 | 127.3 | 127.1 | 130.5 |
| 3''', 5''' | 8.19 (d, 8.78) | 8.18 (d, 8.79) | 8.19 (d, 8.41) | 8.17 (d, 7.88) | 122.8 | 122.9 | 123.0 | 124.4 |
| 4''' | — | — | — | — | 146.3[c] | 146.3 | 146.3 | 148.2 |
| 1' | — | — | — | — | 157.2 | 156.9 | 157.3 | 158.9 |
| 2', 6' | 6.98 (dd, 8.6, 2.37) | 6.96 (d, 8.78) | 6.99 (d, 8.78) | 6.90–7.05 (m) | 114.3 | 114.5 | 114.5 | 115.7 |
| 3', 5' | 7.32 (dd, 8.7, 2.36) | 7.29 (t, 8.79) | 7.35 (t, 8.05) | 7.29 (t, 8.19) | 129.1 | 129.3 | 129.2 | 128.4 |
| 4' | 7.01 (dd, 8.6, 2.36) | 7.01 (d, 8.79) | 6.98 (d, 8.78) | 6.90–7.05 (m) | 120.9 | 121.3 | 121.1 | 122.2 |
| 9-NHCO | 9.10 (d, 7.34) | 8.09 (d, 8.78) | 8.85 (d, 8.05) | 8.90 (d, 7.54) | — | — | — | — |

[a]:$^1$H and $^{13}$C NMR spectra were recorded on a Bruker DRX-200 spectrometer at 200 and 50 MHz respectively in DMSO-d6 as solvent at 393° K. Chemical shifts (δH and δC) are expressed in parts per million with respect to DMSO-d6 as the internal reference.
[b]:Assignments were done by DEPT-135, CHCORR experiments and by comparison of shifts with model compounds having appropriate partial structures.
[c]:Assignments may be interchangeable.
[d]:For compounds (I + II)–4 this carbon appears at 104, 104.8, 103.6 and 104 ppm respectively.
[e]:Coupling constant could not be determined since the other arm of the doublet was embedded under the H2O signal coming from DMSO-d6.
[f]:The C-2 carbon of the free sulfone 3 appears at 55.2 ppm From the spectroscopic findings specially from NMR and other data it would be obvious that sulfoxide (I+II) made by the process described in the present invention is distinct from the sulfoxide obtained earlier by the previous workers which was beta isomer i.e. 1S-isomer of I.

Further, the IR spectrum of the sulfoxide (I+II) revealed it to be the Z-rotamer and it could be converted to the E rotamer by the method described in U.S. Pat. No. 5,410,044 and this rotamer is different from the parent compound in IR and melting point. It is also different from the E rotamer of beta sulfoxide i.e. 1S-isomer of I. The E rotamer of p-nitrobenzyl (1R,6R,7R)-7-phenoxyacetamido-3-hydroxy-3-cephem-4-carboxylate-1-oxide is prepared, for example, by treating the corresponding keto-enol tautomeric mixture (I+II) with or without an alkali in a highly polar solvent such as dimethyl sulfoxide (DMSO).

The following Table III gives comparative properties of four rotamers i.e two from the beta sulfoxide isomer and two from the alpha sulfoxide isomer.

TABLE III

| PROPERTY | I-S Sulfoxide (beta sulfoxide 2) | | I-R Sulfoxide (alpha sulfoxide I + II) | |
|---|---|---|---|---|
| | Z-rotamer | E-rotamer | Z-rotamer | E-rotamer |
| (i) Mt. Pt. (°C.) | 171–173 | 116–120 | 196–197 | 111–115 |
| (ii) $[\alpha]_D^{25}$ (1% in DMF) | +26.4 | +18.1 | –75.8 | –53.0 |

It has been observed that selection of solvent is important for obtaining (I+II) from the starting material III (R=phenoxyacetamido; R1=p-nitrobenzyl). For instance when ozonolysis is conducted in methylene chloride III gives 4 in 90% yield at –85° to –90° C., whereas in acetone (I+II) is obtained in 95% yield under the same reaction conditions. It had been found acetone and methyl ethyl ketone are the best solvents for stereospecific synthesis of (I+II) from III (R=$C_6H_5OCH_2$, R1=p-nitrobenzyl) in maximum yields. Any dilution of the solvent with any other solvents like methylene chloride or ethyl acetate tends to give lower yields of (I+II).

The product obtained by ozonolysis of p-nitrobenzyl 7-phenoxyacetamido-3-exomethylene-cepham-4-carboxylate(III) in methylene chloride when further treated with phosphorous trichloride and dimethyl formamide takes about 4 hours to get converted to the p-nitrobenzyl-7-phenoxyacetamido-3-chloro-3-cephem-4-carboxylate(5), which is also associated with other impurities. But with (I+II) obtained, from ozonisation of III(R=phenoxyacetamido; R1=p-nitrobenzyl), it takes only 2 hours 15 minutes to get the corresponding 3-chloro derivative of I and also in better yields.

This is an additional advantage of (I+II) when used as an intermediate for cefaclor.

The following examples illustrate the invention but these do not limit the scope of the invention. The melting points shown in the examples especially for the mixtures of compounds I+II are of the crude mixture before purification.

It is evident from the experimental that where acetone is used as the solvent in combination with a protic solvent like methanol or acetic acid the title compound is obtained in high yield as demonstrated in examples 1–7 (without use of dimetylsulfide (DMS) and 11–24 (with use of dimethylsulfide (DMS).

EXAMPLES
Without use of DMS

Example 1 p-nitrobenzyl 7-phenoxyacetamido-3-hydroxy-3-cepham-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(40:1)

A solution of 5 g (10.34 mmol) of paranitrobenzyl 7-phenoxyacetamido-3-exomethylene-cepham-4-carboxylate in 200 ml of acetone and 5 ml of methanol is treated with an ozone-oxygen mixture containing 2.083 mmole of ozone per minute at –90° C. for 25 minutes.

To this is added slowly 200 ml of di-isopropyl ether at room temperature and the precipitated white solid is filtered, washed with 10 ml of di-isopropyl ether and the solid obtained is dried under vacuo at 40° C. for 2 hours to afford 3 gm of the title compound as a 3:1 mixture of components I and II respectively. Melting point 188°–190° C.; $[\alpha]_D^{20}$= –80° (C.=1% DMF).

Example 2 p-nitrobenzyl 7-phenoxyacetamido-3-hydroxy-3-cepham-4-carboxylate-1(R)-oxide(I)and p-nitrbenzyl-7-phenoxyaaetamido-3-oxo-3-cepham-4-carboxylate-1(R)-oxide(II).

Ozonolysis in acetone-methanol mixture(30:1)

The solution of 5.0 g (10:34 mmol) of p-nitrobenzyl 7-phenoxyacetamido-3-exomethylene-cepham-4-carboxylate in 150 ml of acetone and 5.0 ml of methanol is treated with 4.5 to 5.0 equivalents of ozone at –60° C. The reaction mixture is slowly warmed to room temperature and stirred at the same temperature for 3 hours. To this is added slowly 450 ml of di-isoprpyl ether, and the solids filtered to afford 3.25 g of the Title Compounds as a 3:1 mixture of components I and II respectively. Melting point 185°–187° C. $[\alpha]_D^{20}$=–78° (C.=1% in DMF).

Example 3 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(30:1)

A solution of 10 g (20.70 mmol) of p-nitro benzyl 7-phenoxyacetamido-3-exomethylene-cepham-4-carboxylate in a mixture of 300 ml acetone and 10 ml methanol is treated at –60° C. for 135 minutes with a stream of oxygen and ozone containing 42.9 mmoles/hr ozone. The reaction mixture is allowed to attain room temperature, and then concentrated to 50 ml under reduced pressure. To this was added 300 ml of di-isopropyl ether dropwise over 30 minutes. The product separated out is filtered and dried under vacuum at 45° C. to give 9.5 g of the title compounds as a 3:1 mixture of components I and II respectively. Melting point 180°–181° C.; $[\alpha]_D^{20}$=–75° (C.=1% DMF Solution).

Example 4 p-nitrobenzyl 7-phenoxyacetamido-3-hydroxy-3-cepham-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(30:1)

A solution of 10 g (20.70 mmoles) of p-nitrobenzyl 7-phenoxyacetamido-3-exomethylene-cepham-4-carboxylate in 300 ml of acetone and 10 ml methanol is treated with a stream of oxygen and ozone containing 0.7 mmol/min of ozone for 120 minutes at −60° C. The reaction mixture is allowed to attain room temperature and the solid obtained was filtered to afford 2.5 g of the title compounds in a 3:1 ratio.

The filtrate is concentrated to 50 ml and to the thick mass is added 300 ml of di-isopropyl ether. A yellowish white amorphous solid separates out which is filtered to give 7.5 g of second crop, which is also a mixture of title compounds as a 3:1 mixture of components I and II respectively. Melting point 178°–180° C.; $[\alpha]_D^{20}$=−63.7° (C.=1% solution in DMF).

Example 5 p-nitrobenzyl-7-phenoxyacetamido-3-hydroxy-3-cepham-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(30:1)

A solution of 10 g (20.7 mmoles) of p-nitrobenzyl-7-phenoxyacetamido-3-exomethylene-cepham-4-carboxylate in 300 ml of acetone and 10 ml of methanol is treated for 105 minutes at −60° C. with a stream of oxygen and ozone, containing 1.39 mmole/min of ozone.

The reaction mixture is allowed to attain room temperature and concentrated to 50 ml under reduced pressure. To this is added 300 ml of di-isopropyl ether at room temperature. The amorphous white solid is filtered and washed with 10 ml di-isopropyl ether and dried under vacuo for 2 hours at 40° C. to yield 8.6 g of the title compounds as a 3:1 mixture of components I and II respectively. Melting point 180°–181° C., $[a]_D^2$=75.60° (C.=1% in DMF).

Example 6 p-nitrobenzyl 7-phenoxyacetamido-3-hydroxy-3-cepham-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(30:1)

A solution of 10 g (20.7 mmoles) of p-nitrobenzyl 7-phenoxyacetamido-3-exomethylene-cepham-4-carboxylate, in 300 ml acetone and 10 ml methanol is treated for 105 minutes at −60° C. with a stream of oxygen and ozone, containing 0.7 mmole/min of ozone. The temperature of the reaction mixture is slowly raised to room temperature. The reaction mixture is evaporated to 50 ml under reduced pressure. To the concentrated residue 300 ml of di-isopropyl ether is added at room temperature. The amorphous white solid is filtered and washed with 10 ml di-isopropylether and dried under vacuo for 2 hrs at 40° C. to afford 9.5 g of the title compounds as a 3:1 mixture of components I and II respectively. Melting point=180°–182° C.; $[\alpha]_D^{20}$=−75.6° (C.=1% in DMF).

Example 7 p-nitrobenzyl 7-phenoxyacetamido-3-hydroxy-3-cepham-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture(30:1)

A solution of 10 g (20.7 mmole) of p-nitrobenzyl-7-phenoxyacetamido-3-exomethylene-cepham-4-carboxylate in 300 ml of acetone and 10 ml of methanol is treated for 105 minutes at −60° C., with a stream of oxygen and ozone containing 0.8 mmole/min of ozone. The mixture is allowed to attain room temperature and concentrated to 75 ml under reduced pressure. To the concentrated residue 300 ml of di-isopropyl ether is added at room temperature. The amorphous solid is filtered, washed with 10 ml di-isopropyl ether and dried under vacuo for 2 hours at 40° C. to afford 9.5 g of crystalline mixture of title compounds as a 3:1 mixture of components I and II respectively. Melting point 186°–189° C.

Example 8

Preparation of p-nitrobenzyl 7-phenoxyacetamido-3-hydroxy-3-cephem-4-carboxylate(4)

Ozonolysis in dichloromethane

A solution of 5 g (10.35 mmol) of p-nitrobenzyl 7-phenoxyacetamido-3-exomethylene-cepham-4-carboxylate in 150 ml of dichloromethane is treated with a stream of oxygen and ozone containing 63 mmoles/hr of ozone for 25 minutes at −90° C. The excess ozone is driven off with oxygen and the HPLC analysis of the reaction mixture indicates a mixture of p-nitrobenzyl esters of 7-phenoxy-acetamido-3-hydroxy-3-cephem-4-carboxylate-1(S)-oxide (2), a mixture of 7-phenoxy acetamido-3-hydroxy-3-cephem-4-carboxylate-1(R)-oxide(I) and 7-phenoxyacetamido-3-oxo-3-cepham-4-carboxylate-1(R)-oxide(II) and 7-phenoxyacetamido-3-hydroxy-3-cephem-4-carboxylate(4) in a ratio of 1.0:2.8:28.0.

Subsequently, the reaction mixture is treated with 1.8 g (8.64 mmol) of phosphorous trichloride, wherein HPLC analysis indicates the ratio of the above mentioned mixture of products to be 1.0:1.5:30.2.

The reaction mixture is thereafter washed with water (3×50 ml) and the organic layer dried over anhydrous sodium sulfate. The dichloromethane solution is evaporated to 50 ml under reduced pressure and to this is added 400 ml of di-isopropyl ether dropwise. The precipitated solid is filtered, washed with cold methanol (2×10 ml) and di-isopropyl ether (50 ml) to give 3 g of the Title compound, existing as a mixture of keto-enol tautomers in a 1:3 ratio. Melting point 108°–110° C. Physico chemical properties are given in Table I.

$^1$H NMR (200 MHz, DMSO-d$_6$); $\delta_H$ 9.21 (d), 9.10 (d), 8.29 (m), 7.90 (d), 7.33 (t), 6.98 (m), 5.73 (s), 5.40 (m), 4.68 (m), 4.20(d), 3.78 (d), 3.15 (d). The two amide signals at 9.21 and 9.10 were present in an integration ratio of 1:3 respectively.

$^{13}$CNMR (50 MHz, DMSO-d$_6$): $\delta_C$ 196.6, 169.5, 169.4, 168.2, 167.1, 165.6, 158.8, 148.1, 144.9, 144.1, 130.5, 130.1, 129.6, 129.2, 124.6, 122.3, 115.8, 103.8, 68.4, 67.5, 67.0, 65.7,63.6,62.2, 60.6, 57.4, 33.5, 28.4, 23.9.

Example 9

Preparation of p-nitrobenzyl 7-phenoxy acetamido-3-hydroxy-3-cephem-4-carboxylate(4)

Ozonolysis in dichloromethane

A solution of 5 g (10.35 mmol) of p-nitrobenzyl 7-phenoxyacetamido-3-exomethylene cepham-4-carboxylate in 200 ml of dichloromethane is treated with a stream of oxygen and ozone containing 70 mmoles/hr of ozone for 25 mins at −90° C. The excess ozone is driven off with oxygen and the reaction mixture containing p-nitrobenzyl esters of 7-phenoxyacetamido-3-hydroxy-3-cephem-4-carboxylate-1(S)-oxide (2), a mixture of 7-phenoxy acetamido-3-hydroxy-3-cephem-4-carboxylate-1(R)-oxide(I) and 7-phenoxyacetamido-3-oxo-3-cepham-4-carboxylate- 1(R)oxide(II) and 7-phenoxyacetamido-3-hydroxy-3-cephem-4-carboxylate in a ratio of 1.0:6.1:58.5, is treated with 1.01 ml (4.68 mmmol) of phosphorus trichloride dissoved in 10 ml of dichloromethane. The reaction mixture is allowed to attain room temperature, wherein HPLC ratio of the above mentioned mixture becomes 1.0:2.0:88.0.

The dichloromethane solution is washed with 100 ml of 5% aqueous sodium bicarbonate solution followed by saturated aqueous NaCl solution and finally with 100 ml water. It is then dried over anhydrous sodium sulfate and filtered off. The clear dichlotomethane solution is diluted with an equal volume of hexane and stirred with 15 g of silica gel for one hour. The mixture is filtered from silica gel and the filtrate evaporated to dryness. The residue obtained is crystallised from methanol to afford 2.5 g of the Title Compound existing as a tautomeric keto-enol mixture in 1:3 ratio. Melting point 110° C.–112° C.

Example 9A p-nitrobenzyl-7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture (40:1)

A solution of 10 gm (20.70 mmole) of p-nitrobenzyl-7-phenoxyacetamido-3-exomethylene-cepham-4-carboxylate in a mixture of 400 ml acetone and 10 ml methanol is treated at −40° C. for 2.5 hours with a stream of oxygen and ozone containing 42.9 mmoles/hr ozone. The reaction mixture is allowed to attain room temperature and stirred at the same temperature for 3 hours. To this is added slowly 450 ml of di-isopropyl ether, and the solids filtered to afford 7.2 g of the title compound as a 3:1 mixture of components I and II respectively. Melting point 186°–188° C.; $[\alpha]_D^{20}$=−75° (C.= 1% in DMF).

Example 9B p-nitrobenzyl-7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture (30:1)

A solution of 10 gm (20.70 mmole) of p-nitrobenzyl-7-phenoxyacetamido-3-exomethylene-cepham-4-carboxylate in a mixture of 300 ml acetone and 10 ml methanol is treated at −40° C. for 2.55 hours with a stream of oxygen and ozone containing 42.9 mmoles/hr ozone. The reaction mixture is allowed to attain room temperature and then concentrated to 50 ml under reduced pressure. To this is added slowly 300 ml of di-isopropyl ether dropwise over 30 minutes at room temperature. The product separated out is filtered and dried under vacuum, at 45° C. to give 8.21 gm of the title compound as a 3:1 mixture of components I and II respectively. Melting point 188°–190° C.; $[\alpha]_D^{20}$=−76° (C.=1% in DMF).
With use of DMS Example 10 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture (40:1)

A solution of 5.6 g (11.59 mmol) of p-nitrobenzyl 7-phenoxyacetamido-3-exomethylene-cepham-4-carboxylate in 224 ml of acetone and 5.6 ml methanol is treated with a stream of oxygen and ozone containing 2.085 mmoles/minute of ozone for 24 minutes at −90° C. To the reaction mixture is added 0.56 ml (7.62 mmol) of dimethyl sulfide and stirred for half an hour at the same temperature and then for 2 hours at room temperature. The reaction mixture is evaporated to 33.6 ml under reduced pressure. To the thick mass is added 168 ml of di-isopropyl ether at room temperature. The amorphous white solids are filtered and washed with 20 ml of di-isopropyl ether and dried under vacuo for 2 hours at 40° C. to yield 4.81 g of title compound as a 3:1 mixture of components I and II respectively.

Melting point 186°–189° C. $[\alpha]_D^{20}$=−80° (C.=1% DMF solution) m/z=500 (M-1)+. The physico-chemical properties are given in Table I. $^1$HNMR (200 MHz, DMSO-d6): $\delta$H 9.38 (d),9.26(d), 8.25 (d), 7.70 (d), 7.32 (t), 6.95 (t), 5.40 (m), 4.62 (m), 4.15 (d), 3.95 (d). The two amide signals at 9.38 and 9.26 are present in an integration ratio of 1:3.

$^{13}$CNMR (50 MHz, DMSO-d6): $\delta$C 193.5, 169.9, 169.5, 164.8, 164.3, 163.5, 163.1., 162.2, 157.1, 146.8, 143.7, 142.6, 129.2, 128.3, 127.8, 123.2, 121.2, 114.5, 102.5, 81.0, 77.3, 66.1, 65.7, 64.2, 62.3, 60.3, 59.3, 56.3, 51.2, 41.7.

Example 11

Preparation of p-nitrobenzyl 7-phenoxyacetamido-3-exomethylene -cepham-4-carboxylate.

200 ml of N,N-dimethylacetamide is cooled to −20° C. with liquid nitrogen-methanol bath. To this is added 3.92 ml (44.81 mmol) of phosphorus trichloride followed by 20 g (40.04 mmol) of p-nitrobenzyl 7-phenoxy acetamido-3-exomethylene-cepham-4-carboxylate-1(S)-oxide. The reaction mixture is stirred for one hour at −20° to −15° C. The reaction mixture is quenched with 400 ml of water and warmed to 40° C., and stirred for half an hour at this temperature. The solids on filtration and washing the cake with 2×50 ml of water and then with 2×50 ml of methanol gave 17.6 g (90.91%) of p-nitrobenzyl 7-phenoxyacetamido-3-exomethylene-cepham-4-carboxylate.

Melting point 146° C., $[\alpha]_D^{20}$=+43.78° (C.=1% DMF solution).

Example 12 p-nitrobenzyl 7-phenoxyacetamido-3-hydroxy-3-cephem-4-carboxylate-1(S)-oxide (2).

Ozonolysis in acetone-acetic acid mixture (120:1)

A solution of 5.0 g (10.01 mmol) of p-nitrobenzyl 7-phenoxyacetamido-3-exomethylene-cepham-4-carboxylate-1(S)-oxide in 300 ml of acetone and 2.5 ml of acetic acid is treated with a stream of oxygen and ozone containing 1.04 mmoles/minute of ozone for 24 minutes at −60° C. To the reaction mixture is added 1.0 ml of dimethyl sulfide and stirred for half an hour at −50° C. and then for 2 hours at room temperature. The reaction mixture is again cooled to 0° C. and the precipitated solids are filtered to afford 4.11 g of p-nitrobenzyl 7-phenoxyacetamido-3-hydroxy-3-cephem-4-carboxylate-1(S)-oxide.

Melting point 171°–173° C., $[\alpha]_D^{20}$=+27.1° (C.=1% in DMF). The compound has HPLC purity of 98%. m/z=502 (M+H)$^+$. Physico-chemical properties are given in Table-I.

$^1$HNMR (200 MHz, DMSO-d6): $\delta$H 8.25 (d), 8.14 (d), 7.75 (d), 7.31 (t), 7.00 (m), 5.90 (m), 5.50 (q), 5.04 (d), 4.68 (s), 4.08 (s).

$^{13}$CNMR (50 MHz, DMSO-d6): $\delta$C 169.3, 165.9, 165.3, 158.3, 156.3, 148.1, 144.4, 130.7, 129.3, 124.5, 122.6, 115.7, 104.8, 67.9, 67.6, 66.5, 57.3, 47.1.

Example 13 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II)

Ozonolysis in acetone-acetic acid mixture (40:1)

A solution of 4.2 g (8.686 mmol) of p-nitrobenzyl 7-phenoxyacetamido-3-exomethylene-cepham-4-carboxylate in 168 ml of acetone and 4.2 ml of acetic acid is treated for 21 minutes at −90° C. with a stream of oxygen and ozone, containing 2.085 mmol/min of ozone. The reaction mixture is treated with 0.42 ml (5.725 mmol) of dimethylsulfide and is stirred for 45 minutes at −90° C. and then for 2.0 hours at room temperature and evaporated to 25.2 ml under reduced pressure. The thick mass is treated with 126 ml of di-isopropyl ether at room temperature. The white solid is filtered and washed with 20 ml of di-isopropyl ether and the compound dried under vacuo for 2.0 hours at 40° C. to afford 3.36 g of the title compound as a 3:1 mixture of components I and II respectively.

Melting point=185°–188° C., $[\alpha]_D^{20}$=−80° (C.=1.0% in DMF). The product is identical to that obtained in Example No. 10 in all other respects like $^1$H NMR, $^{13}$C NMR, IR and UV.

Example 14 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (40:1)

A solution of 3.8 g (7.859 mmol) of p-nitrobenzyl 7-phenoxyacetamido-3-hydroxy-3-cephem-4-carboxylate in 152 ml of acetone and 3.8 ml acetic acid is treated with an oxygen-ozone stream, containing 2.08 mmol of ozone/minute, for 10 minutes at −85° C. After 45 minutes, 0.76 ml (10.34 mmol) of dimethyl sulfide is added to the reaction mixture, which is stirred for 30 minutes at −85° C. and for 2 hours at room temperature and then the solids filtered, to afford 1.3 g of the said compound mixture of enol and keto forms (3:1 ratio). The mother liquor is concentrated to 15.2 ml under reduced pressure. To this is added 76 ml of di-isopropyl ether, the precipitated solid filtered to afford further 1.17 g of the title compound as a 3:1 mixture of components I and II respectively.

Example 15 p-nitrobenzyl 7-phenoxyacetamido-3-hydroxy-3-cephem-4-carboxylate-1(R)-oxide(I) and p-nitrobenzyl 7-phenoxyacetamido-3-oxo-3-cepham-4-carboxylate-1(R)-oxide(II)

Ozonolysis in acetone

A solution of 5.0 g (10.34 mmol) of 7-phenoxyacetamido-3-exomethylene-cepham-4-carboxylic acid-p-nitrobenzyl ester in 200 ml of acetone is treated with an oxygen-ozone mixture at −90° C. until a blue colouration starts to appear. The excess ozone is driven off with oxygen; 0.5 ml (6.80 mmol) of dimethyl sulfide is added and the mixture is stirred for 30 minutes at −80° C. and then for 90 minutes at room temperature. The reaction mixture is then evaporated to 30 ml under reduced pressure. To the thick mass is added 150 ml of di-isopropylether whilst stirring vigorously. The precipitated solids are filtered and washed with 20 ml of di-isopropyl ether. The solids on drying under vacuo at 40° C. for 2.0 hours give 3.92 g of the title compound as a 3:1 mixture of components I and II respectively.

Melting point 187°–189° C., $[\alpha]_D^{20}$ −80.7° (C.=1% in DMF). The product is identical in all respects to those obtained in previous examples.

Example 16 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone

A mixture of 3.8 g (7.859 mmol) of 7-phenoxyacetamido-3-exomethylene-cepham-4-carboxylic acid p-nitrobenzyl ester and 152 ml of acetone is treated, at −90° C. with 4.0 to 4.5 equivalents of ozone according to the process described in the preceding examples. 0.76 ml (10.36 mmol) of dimethyl sulfide is subsequently added and the mixture is stirred for 30 minutes at −80° C. and for 2 hours at room temperature and the solids filtered to afford 1.52 g of the title compound as a 3:1 mixture of components I and II respectively. Melting point 188°–190° C., $[\alpha]_D^{25}$=−75.2° (C.=1% in DMF).

Example 17 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone

A solution of 3.8 g (7.859 mmol) of 7-phenoxyacetamido-3-exomethylene-cepham-4-carboxylic acid-p-nitrobenzyl ester in 228 ml of acetone is treated with an oxygen-ozone mixture containing 2.083 mmol of ozone per minute at −90° C. until a blue colouration persists in the solution. The excess ozone is driven off with oxygen. The reaction mixture thereafter is treated with 0.49 ml (6.68 mmol) of dimethyl sulfide, stirred for 30 minutes at −80° C. and for one hour at room temperature. The reaction mixture is filtered to afford 1.38 g of the title compounds in 3:1 ratio. The mother liquor is concentrated to 15.2 ml and to this is slowly added 72 ml of di-isopropyl ether. The white solids are filtered to afford another 1.30 g of the Title Compound as a 3:1 mixture of components I and II respectively. Melting point 189° C., $[\alpha]_D^{25}$=−75° (1% in DMF solution)

Example 18 p-nitrobenzyl 7-phenoxyacetamido-3-hydroxy-3-cephem-4-carboxylate-1(R)-oxide(I) and p-nitrobenzyl 7-phenoxyacetamido-3-oxo-3-cepham-4-carboxylate-1(R)-oxide(II).

Ozonolysis in acetone-methanol mixture (40:1)

A solution of 3.8 g (7.859 mmol) of 7-phenoxyacetamido-3-exomethylene-cepham-4-carboxylic acid-p-nitrobenzyl ester in 152 ml of acetone and 3.8 ml of methanol is treated with an oxygen-ozone mixture containing 2.083 mmol of ozone per minute at −60° C. until a blue colouration persists in the solution. The reaction mixture thereafter is treated with 0.64 ml (8.724 mmol) of dimethyl sulfide, stirred for 30 minutes at −50° C. and two hours at room temperature and evaporated under reduced pressure to 19 ml. To this is slowly added 114 ml of di-isopropyl ether at room temperature. The precipitated solids on filtration afford 3.07 g of the Title Compound as a 3:1 mixture of components I and II respectively.

Example 19 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-methanol mixture (40:1)

A mixture of 3.8 g (7.859 mmol) of p-nitrobenzyl 7-phenoxyacetamido-3-exomethylene-cepham-4-carboxylate, 152 ml of acetone and 3.8 ml of methanol are treated at −60° C., with 4.0 to 4.5 equivalents of ozone according to the process described in the preceding examples. To this 0.76 ml (10.36 mmol) of dimethyl sulfide is added and the mixture is stirred for 30 minutes at −50° C. and 1.5 hours at room temperature and filtered to obtain 1.358 g of the solids. The resultant mother liquor is concentrated under reduced pressure to 19 ml and to this is slowly added 114 ml of di-isopropyl ether at room temperature. The solids are filtered and washed with 15 ml of di-isopropyl ether, to afford another 1.56 g of the Title Compound as a 3:1 mixture of components I and II respectively.

Melting point 186°–187° C., $[\alpha]D^{20}$=−70.2° (C.=1% in DMF).

Example 20 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone methanol mixture (30:1)

A solution of 4.2 g (8.68 mmol) of p-nitrobenzyl 7-phenoxyacetamido-3-exomethylene-cepham-4-carboxylate in 126 ml of acetone and 4.2 ml of methanol is treated, at −60° C., with 4.0 to 5.0 equivalents of ozone according to the process described in the preceding examples. To this 0.75 ml (10.22 mmol) of dimethyl sulfide is added and the mixture is stirred for 30 minutes at −50° C. and 2.0 hours at room temperature. The reaction mixture is filtered to give 1.40 g of the Title compound as a 3:1 mixture of components I and II respectively. The resultant mother liquor is concentrated under reduced pressure to 16.8 ml and to this is added 84 ml of di-isopropyl ether to afford additional 1.91 g of the title compound as a 3:1 mixture of components I and II respectively.

Melting point 186°–188° C., $[\alpha]_D^{20}$=−79° (C.=1% DMF solution).

Example 21 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (80:1)

An oxygen-ozone stream, containing 1.34 mmol of ozone per minute, is passed for 20 minutes into a solution, cooled to −60° C., of 3.8 g (7.85 mmol) of p-nitrobenzyl 7-phenoxyacetamido-3-exomethylene-cepham-4-carboxylate in 152 ml acetone and 1.9 ml of acetic acid. The excess ozone is driven off with oxygen; 0.45 ml (6.13 mmol) of dimethyl sulfide is added to the reaction mixture, which is stirred for 30 minutes at −50° C. and for 2.0 hours at room temperature and then evaporated to dryness under reduced pressure. 10 ml of methanol is added and the resultant slurry is filtered to give 2.77 g of the Title Compound as a 3:1 mixture of components I and II respectively.

Melting point 188°–190° C.; $[\alpha]_D^{20}$ =−79.1° [C.=1% DMF solution].

Example 22 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (80:1)

A solution of 5.0 gm (10.34 mmol) of p-nitrobenzyl 7-phenoxyacetamido-3-exomethylene-cepham-4-carboxylate in 200 ml of acetone and 2.5 ml of acetic acid is treated with an oxygen-ozone mixture, containing 4.29 mmol of ozone per minute, at −60° C. until a blue colouration starts to appear. The excess ozone is driven off with oxygen; 0.7 ml (9.54 mmol) of dimethyl sulfide is added and the mixture is stirred for 30 mins at −50° C. and for 2.0 hours at room temperature. The reaction mixture is then filtered, to give 2.05 g of the Title Compounds. The resultant mother liquor is concentrated under reduced pressure to 20 ml, then slowly added 250 ml of di-isopropyl ether, filtered the solids to afford another 2.05 g of the title compound as a 3:1 mixture of components I and II respectively.

Example 23 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (80:1)

A mixture of 5.6 g (11.58 mmol) of p-nitrobenzyl 7-phenoxyacetamido-3-exomethylene-cepham-4-carboxylate in 224 ml of acetone and 2.8 ml of acetic acid are treated with an oxygen-ozone mixture at −40° C. until a blue colouration appears. The excess ozone is expelled with oxygen. The reaction mixture is treated with 0.89 ml (12.13 mmol) of dimethyl sulfide and the mixture is stirred for 30 minutes at −35° C. and one hour at room temperature, and the mixture is left to stand over night at room temperature. The solvent is evaporated under reduced pressure to 78 ml, and is cooled to −10° C., and then solid filtered and washed with 10 ml of cold acetone and dried under vacuum for 2.0 hours at 40° C. to give 2.81 g of the title compound as a 3:1 mixture of components I and II respectively. Melting point 187°–189° C., $[\alpha]_D^{25}$=−69° (C.=1% in DMF).

Example 24 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (80:1)

A mixture of 5.6 g (11.58 mmol) of p-nitrobenzyl 7-phenoxyacetamido-3-exomethylene-cepham-4-carboxylate, 224 ml of acetone and 2.8 ml of acetic acid are treated for 62 minutes, at −25° C. with an oxygen-ozone mixture, containing 1.73 mmol of ozone per minute, and is then treated with 1.12 ml (15.26 mmol) of dimethyl sulfide at −25° C. The mixture is stirred for 30 minutes at −20° C.

and for one hour at room temperature, and the mixture cooled to −10° C. The precipitated solids are filtered (1.2 g). The resulting mother liquor is evaporated under reduced pressure. To this is added 100 ml of di-isopropyl ether and the solids filtered to afford another 0.42 g of crystalline material. The two crops together contain the Title Compound as a 3:1 mixture of components I and II respectively. Melting point 176°–177° C., $[\alpha]_D^{20}=-71°$ (C.=1% in DMF).

Example 25 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in Acetone-Dichloromethane mixture (1:1)

A mixture of 5.0 g (10.34 mmol) of p-nitrobenzyl 7-phenoxyacetamido-3-exomethylene-cepham-4-carboxylate, 75 ml of acetone, 75 ml of dichloromethane and 5 ml of methanol are treated, at −60° C., with 4.5 to 5.0 equivalents of ozone according to the process described in the preceding examples. 1.0 ml (13.63 mmol) of dimethyl sulfide is added and the mixture is stirred for 30 minutes at −50° C. and for one hour at room temperature. The precipitated solids are filtered to afford 1.52 g of the title compound as a 3:1 mixture of components I and II respectively. The resulting mother liquor is concentrated to 20 ml and to this is slowly added 50 ml of di-isopropylether. The solids are filtered to afford further 2.04 g of the Title Compound as a 3:1 mixture of components I and II respectively. Melting point 181°–183° C., $[\alpha]_D^{20}=-75°$ (C.=1% in DMF).

Example 26 p-nitrobenzyl 7-phenoxyacetamido-3-hydroxy-3-cephem-4-carboxylate-1(R)-oxide(I) and p-nitrobenzyl-7-phenoxyacetamido-3-oxo-3-cepham-4-carboxylate-1(R)-oxide(II).

Ozonolysis in acetone-acetic acid mixture (75:1)

A solution of 10 g (20.70 mmol) of p-nitrobenzyl 7-phenoxyacetamido-3-exomethylene-cepham-4-carboxylate in a mixture of 300 ml acetone and 4 ml acetic acid is treated for 120 minutes at −60° C., with a stream of oxygen and ozone, containing 42.9 mmoles/hr of ozone. The reaction mixture is treated with 1.7 ml dimethyl sulfide and allowed to attain room temperature. 300 ml water is then added dropwise in 30 minutes to precipitate out the solid which is filtered and washed with 10 ml water. The solid is dried under vacuum at 45° C. to give 7.0 g of the Title Compound as a 3:1 mixture of components I and II respectively.

Example 27

Ozonolysis of p-nitrobenzyl-7-phenoxy acetamido-3-exomethylene-cepham-4-carboxylate in Methyl Ethyl Ketone.

A solution of 5.0 g (10.34 mmol) of p-nitrobenzyl 7-phenoxyacetamido-3-exomethylene-cepham-4-carboxylate in 200 ml of Methyl Ethyl Ketone is cooled to −60° C. and is treated with an oxygen-ozone mixture containing 2.08 mmol of ozone per minute until a blue colouration begins to appear. The excess ozone is expelled with oxygen. The reaction mixture is treated with 0.8 ml (10.90 mmol) of dimethyl sulfide and the mixture is stirred for 30 minutes at −50° C. and one hour at room temperature. It is then evaporated under reduced pressure to dryness. To this is added 20 ml of Methyl Ethyl Ketone to dissolve the residue and then added 100 ml of di-isopropyl ether, and the precipitated solids filtered to afford 1.04 g of crystalline product, containing a 1:4 mixture of p-nitrobenzyl 7-phenoxyacetamido-3-hydroxy-3-cephem-4-carboxylate-1 (S)-oxide(2) and a mixture of p-nitrobenzyl 7-phenoxyacetamido-3-hydroxy-3-cephem-4-carboxylate-1 (R)-oxide(I), and 7 phenoxyacetamido-3-oxo-3-cepham-4-carboxylate-1(R)-oxide(II) as determined by NMR and HPLC.

Example 28

Ozonolysis of p-nitrobenzyl-7-phenoxy acetamido-3-exomethylene-cepham-4-carboxylate in Dichloromethane.

Acetone-Dichloromethane mixture (1:4)

A solution of 5.0 g (10.34 mmol) of p-nitrobenzyl 7-phenoxyacetamido-3-exomethylene-cepham-4-carboxylate in 150 ml of dichloromethane and 5.0 ml of methanol is treated for 25 minutes at −60° C. with a stream of oxygen-ozone, containing 2.08 mmol/min of ozone. The excess ozone is driven off with oxygen. 0.7 ml (9.54 mmol) of dimethyl sulfide is added and the reaction mixture is stirred for 30 minutes at −50° C., then for two hours at, room temperature. It is then evaporated under reduced pressure to dryness. The residue is dissolved in 35 ml of dichloromethane, and to this is added 100 ml of di-isopropyl ether, and further evaporated to a gum (1.5 g) containing a mixture of p-nitrobenzyl 7-phenoxyacetamido 3-oxo-3-cepham-4-carboxylate-1(R)- oxide(II), p-nitrobenzyl 7-phenoxyacetamido-3-hydroxy-3-cephem-4-carboxylate-1 (R)-oxide(I) and p-nitrobenzyl 7-phenoxyacetamido-3-hydroxy-3-cephem-4-carboxylate-1(S)-oxide(2), in a ratio of 1.00:3.04:1.73.

Example 29

Ozonolysis of p-nitrobenzyl-7-phenoxy acetamido-3-exomethylene-cepham-4-carboxylate in Acetone-Dichloromethane mixture (1:4).

A mixture of 4.2 g (8.68 mmol) of p-nitrobenzyl 7-phenoxyacetamido-3-exomethylene-cepham-4-carboxylate, 25.2 ml of acetone, 100.8 ml of dichloromethane and 4.2 ml of methanol are treated, at −60° C., with 4.5 to 5.0 equivalents of ozone, until a blue colouration appears. The excess ozone is driven off with oxygen and 0.84 ml (11.45 mmol) of dimethyl sulfide is added and the mixture is stirred for 30 minutes at −50° C. and for two hours at room temperature and is then evaporated to dryness under reduced pressure. The residue is redissolved in a mixture of 8 ml of acetone and 32 ml of dichloromethane. To this is added 100 ml of di-isopropylether at room temperature, and the precipitated solids filtered. 2.80 g of solid containing a mixture of p-nitrobenzyl esters of 7-phenoxyacetamido 3-hydroxy-3-cephem-4-carboxylate-1(S)-oxide(2), 7-phenoxy-acetamido-3-oxo-3-cepham-4-carboxylate-1(R)-oxide(II) and 7-phenoxyacetamido-3-hydroxy-3-cephem-4-carboxylate-1(R)-oxide(I) in a ratio of 1.0:2.1:6.3 as determined by $^1$HNMR and HPLC is obtained.

Example 30

Ozonolysis of p-nitrobenzyl 7-phenoxy acetamido-3-exomethylene-cepham-4-carboxylate in Acetone-Dichloromethane mixture (1:9).

A mixture of 5.6 g (11.58 mmol) of p-nitrobenzyl 7-phenoxyacetamido-3-exomethylene-cepham-4-carboxylate, 16.8 ml of acetone, 151.2 ml of dichloromethane and 5.6 ml of methanol are treated, at −60° C., with an oxygen-ozone mixture, containing 2.08 mmol of ozone per minute, until a blue colouration appears. The excess ozone is driven off with oxygen and 1.12 ml (15.26 mmol) of dimethyl sulfide is added and the mixture is stirred for 30 minute at −50° C. and for one hour at room temperature and is then evaporated under reduced pressure. The residue is dissolved in a mixture of 35 ml of a 1:9 acetone and dichloromethane. To this is added 100 ml of di-isopropyl ether and filtered to give 1.8 g solid containing a mixture of compounds viz p-nitrobenzyl esters of 7-phenoxyacetamido-3-oxo-3-cephem-4-carboxylate-1(R)-oxide (II),7-phenoxyacetamido-3-hydroxy-3-cephem-4-carboxylate-1(R)-oxide(I) and 7-phenoxy acetamido-3-hydroxy-3-cephem-4-carboxylate-1(S)-oxide(2), in a ratio of 1.00:2.94:1.05.

Example 31

Preparation of p-nitrobenzyl 7-phenoxyacetamido-3-hydroxy-3-cephem-4-carboxylate(4)

A solution of 5 g (10.35 mmol) of p-nitrobenzyl 7-phenoxyacetamido-3-exomethylene-cepham-4-carboxylate in 150 ml of dichloromethane is treated with a stream of oxygen and ozone containing 63 mmoles/hr of ozone for 35 mins at −80° C. The excess ozone is driven off with oxygen and the reaction mixture containing p-nitrobenzyl esters of 7-phenoxy-acetamido-3-hydroxy-3-cephem-4-carboxylate-1(S)-oxide(2) and 7-phenoxyacetamido-3-hydroxy-3-cephem-4-carboxylate-1(R)-oxide(I) along with its 3-oxo tautomer(II) and 7-phenoxy acetamido-3-hydroxy-3-cephem-4-carboxylate (4) in an approximate ratio of 1.0:0.7:5.15 (as analysed by HPLC) is treated with 3 ml (40.85 mmol)of dimethylsulfide at −80° C. Thereafter it is stirred for 30 minutes at −80° C. and the temperature is gradually raised to 25° C. HPLC at this stage indicates the above mentioned ratio as 1.0:2.94:34.80. The reaction mixture is washed twice with 100 ml saturated aqueous sodium chloride solution, the dichloromethane layer is dried over anhydrous sodium sulfate and evaporated under reduced pressure to give yellowish white solid. The residue on chromatography over silicagel using dichloromethane-hexane(1:1) as eluent afford 3.0 g of the Title Compound, which exists partially in the keto form.

An approximate keto-enol tautomeric ratio of 1:3 is indicated by NMR, HPLC purity 90%. Melting point 109°–111° C. Physico chemical properties are given in Table I.

Example 32

Sodium salt of p-nitrobenzyl-7-phenoxy acetamido-3-hydroxy-3-cephem-4-carboxylate-1(R)-oxide(Ia).

A mixture of 5.0 g (9.97 mmol) of 7-phenoxyacetamido-cepham-3-one and -3-hydroxy-3-cephem-4-carboxylic acid-p-nitrobenzyl ester-1(R)-oxides, 400 ml of dichloromethane and 400 ml of water is cooled to 0° C., and treated with 40 ml(10 mmol) of 1% solution of sodium hydroxide at 0° C. The reaction mixture is stirred for 15 minutes at 0° C. and the temperature raised to 25° C. The aqueous layer is separated from the organic phase and washed with 50 ml of dichloromethane. The separated aqueous layer is lyophilized, to afford 4.7 g of crystalline sodium salt of 7-phenoxy acetamido-3-hydroxy-3-cephem-4-carboxylic acid p-nitrobenzyl ester-1(R)-oxide.

Melting point 193°–196° C., $[\alpha]_D^{20}$=−19.09° (C.=1% in $H_2O$) and has a HPLC purity of 99.0%. Spectral data are given in Table-II and physico chemical properties in Table-I.

Example 33 p-nitrobenzyl 7-phenoxyacetamido-3-methoxy-3-cephem-4-carboxylate-1(R)-oxide.

A solution of 1.0 g (1.99 mmol) 7-phenoxyacetamido-cepham-3-one and 3-hydroxy-3-cephem-4-carboxylic acid-p-nitrobenzyl ester-1(R)-oxides (1:3 mixture) in 15 ml of methanol is treated at 0° C. with excess of a solution of diazomethane in diethyl ether, until a light yellow colouration persists. The solution is stirred for 15 minutes and subsequently the solvent is evaporated at reduced pressure. The Title Compound is obtained as yellow crystals.

$^1$HNMR (200 MHz, DMSO-d6) δ 3.89 (S,—$OCH_3$, 3H); 4.30 (dd,$C_2H_2$,2H); 4.50–4.60 (m, $PhOCH_2$ & $C_7H$, $C_6H$, 3H); 5.30–5.50 (m, 4($NO_2$) $PhCH_2$ & $C_7H$, 3H); 7.00 (t, 3H); 7.30 (t, 2H); 7.70(d, 2H); 8.20(d, 2H); 9.30 (d, NH, 1H).

Example 34

Sodium salt of p-nitrobenzyl 7-phenoxyacetamido-3-hydroxy-3-cephem-4-carboxylate-1(S)-oxide(2a)

A mixture of 100 mg (1.199 mmol) of p-nitrobenzyl 7-phenoxyacetamido-3-hydroxy-3-cephem-4-carboxylate-1 (S)-oxide, 10 ml of dichloromethane and 10 ml of water is cooled to 0° C. and treated with 0.8 ml (0.2 mmole) of 1% sodium hydroxide solution at 0° C. The mixture is stirred for 15 minutes at 0° C. and the temperature raised to 25° C. The aqueous layer is separated from the organic phase and washed with 50 ml of dichloromethane. The separated aqueous layer is lyophilized to afford 92 mg of sodium salt of 7-phenoxyacetamido-3-hydroxy-3-cephem-4-carboxylic acid p-nitrobenzyl ester-1(S)-oxide (2a).

Melting point 103°–106° C., $[\alpha]_D^{20}$=+102.44° (C.=1% in $H_2O$), HPLC purity=99%. Spectral data are given in Table-II and physico chemical properties in Table-I. Example 35 p-nitrobenzyl 7-phenoxyacetamido-3-exo methylene-cepham-4-carboxylate-1, 1-dioxide To a solution of 10 g (20.04 mmol) of p-nitrobenzyl-7-phenoxyacetamido-3-exomethylene-cepham-4-carboxylate-1(S)-oxide in dichloro methane (100 ml) cooled to 20°–25° C. is added a mixture of 9.2 g (20.04 mmol) formic acid and 6.8 g (60 mmol) of 30% aqueous solution of hydrogen peroxide slowly over one hour maintaining temperature between 20°–25° C. Thereafter the reaction mixture is stirred at the same temperature for 20 hours. The slightly hazy reaction mixture is washed with 2×50 ml water. The dichloro methane layer is dried over anhydrous sodium sulfate and concentrated to dryness under reduced pressure. The solid is triturated with di-isopropyl ether (50 ml) and the crystalline material filtered to afford 9.2 g (89.14%) of the title compound, having a purity of [94]%;$[\alpha]_D^{20}$=−76.22° (C.=1% DMF).

Example 36 p-nitrobenzyl 7-phenoxyacetamido-3-hydroxy-3-cephem-4-carboxylate-1, 1-dioxide.(3)

A solution of 2 g (3.88 mmol) of p-nitrobenzyl 7-phenoxyacetamido-3-exomethylene-cepham-4-carboxylate-1,1-dioxide in 50 ml dichloro methane is cooled to −60° C. A stream of oxygen-ozone mixture equivalent to 2.95 mmol of ozone/hour is passed through the solution for one hour. To this is added dimethyl sulfide 0.34 ml (4.65 mmol) and the solution stirred at −60° C. for 30 minutes and then at 25° C. for 2 hours. The reaction mixture is washed successively with saturated NaCl solution (20 ml), water (20 ml) and the organic layer dried over anhydrous sodium sulfate. Evaporation of dichloromethane under reduced pressure gives 1.9 gm of the title compound as amorphous solid.

Melting point 100°–103° C., m/z=518 (M+H)[30], $[\alpha]_D^{20}$= −38.82° (C.=1% DMF). Physico chemical properties are given in Table-I.

$^1$HNMR(220 MHz, DMSO-$d_6$): δ H8.73(d), 8.25(d), 7.71 (d), 7.30(t), 6.97(m), 5.85(m), 4.30(m), 5.18(d), 4.68(m)

$^{13}$CNMR (200 MHz, DMSO-d6): δ$_C$ 170.3, 166.3, 164.3, 159.7, 158.7, 148.4, 144.9, 130.8, 129.5, 124.8, 122.7, 115.9, 103.6, 69.7, 67.6, 66.3, 59.4, 55.2.

Example 37 p-nitrobenzyl 7-phenoxyacetamido-3-hydroxy-3-cephem-4-carboxylate-1, 1-dioxide.(3)

A solution of 5.0 g (9.97 mmol) of a 3:1 mixture of p-nitrobenzyl 7-phenoxyacetamido-3-hydroxy-3-cephem-4-carboxylate-1(R)-oxide and p-nitrobenzyl 7-phenoxyacetamido-3-oxo-3-cephem-4-carboxylate-1(R)-oxide in 75 ml of chloroform, is treated with 2.3 gm (13.32 mmol) of m-chloroperbenzoic acid at 25° C. and the reaction mixture is warmed to 60° C. and stirred for 80 minutes at 60° C. It is then cooled to room temperature and 200 ml of di-isopropyl ether is added and the precipitated solids filtered to afford 2.0 g of crystalline p-nitrobenzyl-7-phenoxyacetamido-3-hydroxy-3-cephem-4-carboxylate-1, 1-dioxide. Melting point 102°–105° C.; $[\alpha]_D^{20}$=–38.80°. Spectral data are comparable to that obtained in example 36.

Example 38 p-nitrobenzyl 7-phenoxyacetamido-3-hydroxy-3-cephem-4-carboxylate-1,1-dioxide(3).

A solution of 1.0 gm (1.99 mmol) of p-nitrobenzyl 7-phenoxyacetamido-3-hydroxy-3-cephem-4-carboxylate-1 (S)-oxide in 20 ml of chloroform is treated with 0.6 g (3.47 mmol) of m-chloroperbenzoic acid at 25° C. and the reaction mixture is warmed to 60° C. and stirred for 80 minutes at 60° C. It is then cooled to room temperature and 50 ml of di-isopropyl ether is added and the precipitated solids filtered to afford 0.5 gm of crystalline p-nitrobenzyl 7-phenoxyacetamido-3-hydroxy-3-cephem-4-carboxylate-1,1-dioxide, melting point 101°–104° C., and the spectral data is identical in all respects with the product as obtained in example No.36.

Example 39

Sodium salt of p-nitrobenzyl 7-phenoxyacetamido-3-hydroxy-3-cephem-4-carboxylate-1,1-dioxide(3a).

A mixture of 100 mg (0.193 mmol) of p-nitrobenzyl 7-phenoxyacetamido-3-hydroxy-3-cephem-4-carboxylate-1,1-dioxide, 10 ml of dichloromethane and 10 ml of water is cooled to 0° C. and treated with 0.77 ml (0.193 mmol) of 1% sodium hydroxide solution, at 0° C. The reaction mixture is stirred for 15 minutes at 0° C. and the temperature raised to 25° C. The aqueous layer is separated from the organic phase and washed with 20 ml of dichloromethane. The separated aqueous layer is lyophilized to afford 97 mg of sodium salt of p-nitrobenzyl-7-phenoxyacetamido-3-hydroxy-3-cephem-4-carboxylate-1,1-dioxide, melting point 156°–159° C., purity 99%. The spectral properties are given in Table-II and physico chemical properties in Table-I.

Example 40

Sodium salt of p-nitrobenzyl 7-phenoxyacetamido-3-hydroxy-3-cephem-4-carboxylate(4a).

A mixture of 100 mg (0.205 mmol) of p-nitrobenzyl esters of 7-phenoxyacetamido-3-hydroxy-3-cephem and 3-oxo-3-cepham-4-carboxylates, 10 ml of dichloromethane and 10 ml of water is cooled to 0° C. and treated with 0.82 ml (0.206 mmol) of 1% sodium hydroxide solution, at 0° C. The reaction mixture is stirred for 15 minutes at 0° C. and the temperature raised to 25° C. The aqueous layer is separated from the organic phase and washed with 20 ml of dichloromethane. The separated aqueous layer is lyophilized to afford 96 mg of sodium salt of p-nitrobenzyl-7-phenoxyacetamido-3-hydroxy-3-cephem-4-carboxylate, melting point 161°–164° C., purity 99%. The spectral properties are given in Table II and physico chemical properties in Table-I.

Example 41 p-nitrobenzyl 7-phenoxyacetamido-3-hydroxy-3-cephem-4-carboxylate-1,1-dioxide(3).

A solution of 5.0 g (10.3 mmol) of p-nitrobenzyl 7-phenoxyacetamido-3-hydroxy-3-cephem-4-carboxylate in 75 ml of chloroform is treated with 4.6 g (26.65 mmol) of m-chloroperbenzoic acid at 25° C. and the reaction mixture is warmed to 60° C. and stirred for 80 minutes at 60° C. It is then cooled to room temperature and 250 ml of di-isopropyl ether is added and the precipitated solids filtered to afford 1.8 gm of crystalline p-nitrobenzyl 7-phenoxyacetamido-3-hydroxy-3-cephem-4-carboxylate-1,1-dioxide, melting point 99°–101° C., and the spectral data is identical in all respects with the product as obtained in example No.36.

Example 42

Preparation of p-nitrobenzyl 7-phenoxyacetamido-3-chloro-3-cephem-4-carboxylate(5)

General procedure:

This compound was prepared by the procedure described in the literature. See, for example, U.S. Pat. No. 4,115,643.

To a solution of phosphorous trichloride in DMF was added p-nitrobenzyl 7-phenoxyacetamido-3-hydroxy-3-cephem-4-carboxylate its 1(R)-oxide and 1(S)-oxide obtained by ozonolysis of the corresponding exosulfide in dichloromethane, at a temperature of about –30° C. Subsequently, the reaction was continued at +15° C. for 3–4 hours. Thereafter, the reaction mixture was diluted with water at 45°–50° C. The solid obtained is filtered, washed with water and methanol to yield the product.

The comparative data for the preparation of (5) from compounds I and II and the compound obtained by ozonolysis of exosulfide in dichloromethane is shown in Table IV.

TABLE IV

| SUB-STRATE | AMOUNT OF SUB-STRATE (g) | AMOUNT OF DMF (ml) | PCl$_3$ MOLAR EQ | RE-ACTION TIME (HOURS) | PRODUCT YIELD (%) (5) | (4) |
|---|---|---|---|---|---|---|
| I | 4.0 | 60 | 4.0 | 2.15 | 67.63 | <1.0 |
| I | 45 | 675 | 4.0 | 2.30 | 69.75 | <1.0 |
| A | 4.0 | 60 | 4.0 | 4.0 | 61.48 | 2.90 |
| A | 5.0 | 75 | 4.0 | 4.0 | 46.21 | 2.98 |

A — Mixture of p-nitrobenzyl esters of 7-phenoxyacetamido-3-hydroxy-3-cephem-4-carboxylate(4), and its corresponding 1(R)-oxide(I, II) and 1(S)-oxide(2) obtained by ozonolysis of the corresponding 3-exomethylene-cepham derivative in dichloromethane.

Example 43 conversion of a mixture containing the Z-rotamer of P-nitrobenzyl-7-Phenoxyacetamido-3-hydroxy-3-cephem-4-carboxylate-1(R)-oxide (I) and its 3-oxo tautomer (II) into a mixture containing the E-rotamer of the enol.

100 mg of the above mixture was dissolved in 0.9 ml of DMSO at room temperature. To the solution was added 2.5 ml of water slowly under stirring. The precipitated solids were filtered, washed thoroughly with 10 ml of water, followed by 1 ml of methanol. The solids were dried under vacuum for 2 hrs at 40° C. to afford 80 mg of a mixture containing the E-rotamer. The mixture had a melting point of 111°–115° C. and $[\alpha]_D^{25}=-53.0°$ (C.=1% solution in DMF). The IR spectrum of this compound exhibited a broad OH streching in the range 2.89 to 3.17 micron in contrast to a sharp OH signal at 3.02 micron observed for the mixture having the enol tautomer as its Z-rotamer.

We claim:

1. A process for the stereospecific synthesis of a keto-enol tautomeric mixture of p-nitrobenzyl (1R,6R,7R)-7-phenoxyacetamido-3-hydroxy-3-cephem-4-carboxylate-1-oxide of formula I and p-nitrobenzyl (1R,6R,7R)-7-phenoxyacetamido-3-oxo-cepham-4-(R/S)-carboxylate-1-oxide of formula II,

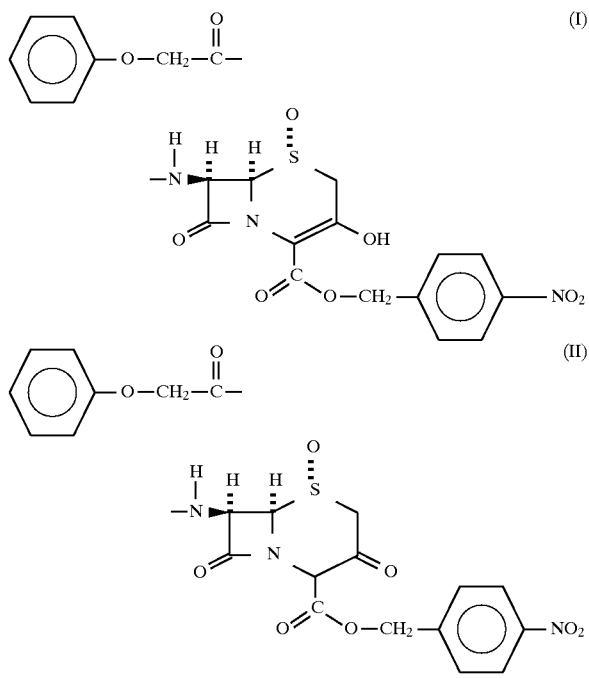

comprising reacting p-nitrobenzyl 7-phenoxyacetamido-3-exomethylene-cepham-4-carboxylate with ozone in an inert organic solvent at a temperature ranging from −90° C. to about −40° C. to form an ozonide and decomposing the ozonide without using a reducing agent.

2. The process according to claim 1, wherein a protic solvent is used with the inert organic solvent in the reaction of p-nitrobenzyl 7-phenoxyacetamido-3-exomethylene-cepham-4-carboxylate with ozone.

3. The process of claim 1, wherein the inert organic solvent is acetone or methyl ethyl ketone.

4. The process of claim 1, wherein the inert organic solvent is acetone.

5. The process of claim 1, wherein acetone and a protic solvent are used.

6. The process of claim 4, wherein the protic solvent is methanol, acetic acid or isopropanol.

7. The process according to claim 2, wherein the protic solvent is methanol, acetic acid or isopropanol.

8. The process according to claim 3, wherein a mixture of the inert organic solvent and protic solvent is used in a ratio ranging from 120:1 to 30:1.

9. The process according to claim 8, wherein the ratio of the inert organic solvent and protic solvent is 40:1.

10. The process according to claim 1, is from the reaction temperature −90° C. to about −65° C.

11. A process of claim 1, further comprising converting p-nitrobenzyl(1R,6R,7R)-7-phenoxyacetamido-3-hydroxy-3-cephem-4-carboxylate-1-oxide and its keto isomer into E-rotamer of p-nitrobenzyl(1R,6R,7R)-7-phenoxyacetamido-3-hydroxy-3-cephem-4-carboxylate-1-oxide by dissolving the p-nitrobenzyl (1R,6R,7R)-7-phenoxyacetamido-3-hydroxy-3-cephem-4-carboxylate-oxide in a highly polar solvent.

12. The process according to claim 11, wherein the highly polar solvent is dimethyl sulfoxide.

* * * * *